(12) United States Patent
Takamura et al.

(10) Patent No.: US 10,576,123 B2
(45) Date of Patent: Mar. 3, 2020

(54) TISSUE OCCLUDING AGENT COMPRISING AN IEIKIEIKIEIKI PEPTIDE

(75) Inventors: Kentaro Takamura, Tokyo (JP); Satoshi Gojo, Saitama (JP); Satoru Kobayashi, Tokyo (JP)

(73) Assignee: 3-D Matrix, Ltd., Tokyo (JP)

( * ) Notice: Subject to any disclaimer, the term of this patent is extended or adjusted under 35 U.S.C. 154(b) by 702 days.

(21) Appl. No.: 13/122,758

(22) PCT Filed: Oct. 6, 2009

(86) PCT No.: PCT/JP2009/067367
§ 371 (c)(1),
(2), (4) Date: Apr. 6, 2011

(87) PCT Pub. No.: WO2010/041636
PCT Pub. Date: Apr. 15, 2010

(65) Prior Publication Data
US 2011/0201541 A1    Aug. 18, 2011

(30) Foreign Application Priority Data

Oct. 6, 2008 (JP) ................ 2008-259860
Dec. 11, 2008 (JP) ................ 2008-316133

(51) Int. Cl.
| | | |
|---|---|---|
| A61K 38/10 | (2006.01) | |
| C07K 7/08 | (2006.01) | |
| A61K 38/16 | (2006.01) | |
| A61L 31/14 | (2006.01) | |
| A61L 31/04 | (2006.01) | |
| A61K 31/7004 | (2006.01) | |
| A61K 31/7016 | (2006.01) | |
| A61K 38/08 | (2019.01) | |
| C07K 7/06 | (2006.01) | |

(52) U.S. Cl.
CPC .......... *A61K 38/10* (2013.01); *A61K 31/7004* (2013.01); *A61K 31/7016* (2013.01); *A61K 38/08* (2013.01); *A61K 38/16* (2013.01); *A61L 31/047* (2013.01); *A61L 31/148* (2013.01); *C07K 7/06* (2013.01); *C07K 7/08* (2013.01); *A61L 2400/04* (2013.01); *A61L 2430/36* (2013.01)

(58) Field of Classification Search
None
See application file for complete search history.

(56) References Cited

U.S. PATENT DOCUMENTS

| | | |
|---|---|---|
| 4,582,640 A | 4/1986 | Smestad et al. |
| 4,642,117 A | 2/1987 | Nguyen et al. |
| 4,947,840 A | 8/1990 | Yannas et al. |
| 5,110,604 A | 5/1992 | Chu et al. |
| 5,126,141 A | 6/1992 | Henry |
| 5,236,903 A | 8/1993 | Saiki et al. |
| 5,292,514 A | 3/1994 | Capecchi et al. |
| 5,510,102 A | 4/1996 | Cochrum |
| 5,527,610 A | 6/1996 | Urry |
| 5,550,187 A | 8/1996 | Rhee et al. |
| 5,670,483 A | 9/1997 | Zhang et al. |
| 5,747,452 A | 5/1998 | Ruoslahti et al. |
| 5,773,577 A | 6/1998 | Cappello |
| 5,955,343 A | 9/1999 | Holmes et al. |
| 6,046,160 A | 4/2000 | Obi-Tabot |
| 6,224,893 B1 | 5/2001 | Langer et al. |
| 6,280,474 B1 | 8/2001 | Cassidy et al. |
| 6,548,630 B1 | 4/2003 | Zhang et al. |
| 6,730,298 B2 | 5/2004 | Griffith-Cima et al. |
| 6,800,481 B1 | 10/2004 | Holmes et al. |
| 7,098,028 B2 | 8/2006 | Holmes et al. |
| 7,449,180 B2 | 11/2008 | Kisiday et al. |
| 7,713,923 B2 | 5/2010 | Genove et al. |
| 7,846,891 B2 | 12/2010 | Ellis-Behnke et al. |
| 8,022,178 B2 | 9/2011 | Horii et al. |
| 9,012,404 B2 | 4/2015 | Spirio et al. |
| 9,084,837 B2 | 7/2015 | Ellis-Behnke et al. |
| 9,162,005 B2 | 10/2015 | Ellis-Behnke et al. |
| 9,327,010 B2 | 5/2016 | Ellis-Behnke et al. |
| 9,339,476 B2 | 5/2016 | Norchi et al. |
| 9,364,513 B2 | 6/2016 | Ellis-Behnke et al. |
| 9,415,084 B2 | 8/2016 | Ellis-Behnke et al. |
| 9,439,941 B2 | 9/2016 | Ellis-Behnke et al. |
| 9,724,448 B2 | 8/2017 | Kobayashi et al. |
| 10,245,299 B2 | 4/2019 | Mehta et al. |
| 10,369,237 B2 | 8/2019 | Gil et al. |
| 2002/0160471 A1 | 10/2002 | Kisiday et al. |
| 2003/0069177 A1* | 4/2003 | Dubaquie et al. ............. 514/12 |
| 2003/0166846 A1 | 9/2003 | Rothstein et al. |
| 2004/0204561 A1 | 10/2004 | Ellison |
| 2004/0242469 A1 | 12/2004 | Lee et al. |
| 2005/0181973 A1 | 8/2005 | Genove et al. |
| 2005/0287186 A1 | 12/2005 | Ellis-Behnke et al. |
| 2006/0084607 A1* | 4/2006 | Spirio et al. ................. 514/13 |
| 2006/0148703 A1 | 7/2006 | Lee et al. |
| 2006/0293243 A1 | 12/2006 | Puri et al. |

(Continued)

FOREIGN PATENT DOCUMENTS

| | | |
|---|---|---|
| CA | 2572964 A1 | 2/2006 |
| CA | 2618184 A1 | 12/2006 |

(Continued)

OTHER PUBLICATIONS

Lee, J., et al. Tissue Eng. (Mar. 2008), 14(1); pp. 61-86.*

(Continued)

*Primary Examiner* — Kevin S Orwig
(74) *Attorney, Agent, or Firm* — Choate, Hall & Stewart LLP

(57) ABSTRACT

There is provided a bioabsorbable peptide tissue occluding agent that can be applied to large mammals including humans, the peptide tissue occluding agent being obtained by artificial synthesis to avoid concerns of infection by viruses and the like. The tissue occluding agent contains a peptide, wherein the peptide is an amphiphilic peptide having 8-200 amino acid residues with the hydrophilic amino acids and hydrophobic amino acids alternately bonded, and is a self-assembling peptide exhibiting a β-structure in aqueous solution in the presence of physiological pH and/or a cation.

4 Claims, 14 Drawing Sheets

Specification includes a Sequence Listing.

(56) References Cited

U.S. PATENT DOCUMENTS

| | | |
|---|---|---|
| 2007/0128175 A1 | 6/2007 | Ozbas et al. |
| 2007/0190603 A1 | 8/2007 | Holmes et al. |
| 2008/0032934 A1* | 2/2008 | Ellis-Behnke et al. ......... 514/13 |
| 2008/0091233 A1 | 4/2008 | Ellis-Behnke et al. |
| 2009/0053103 A1 | 2/2009 | Mortimer et al. |
| 2009/0111734 A1 | 4/2009 | Ellis-Behnke et al. |
| 2009/0162437 A1 | 6/2009 | Horii et al. |
| 2009/0169598 A1 | 7/2009 | Crutcher |
| 2010/0143504 A1 | 6/2010 | Spirio et al. |
| 2010/0311640 A1 | 12/2010 | Genove et al. |
| 2011/0002880 A1 | 1/2011 | Takamura et al. |
| 2012/0010140 A1 | 1/2012 | Ellis-Behnke et al. |
| 2012/0058066 A1 | 3/2012 | Nagai et al. |
| 2013/0281547 A1 | 10/2013 | Spirio et al. |
| 2013/0296239 A1 | 11/2013 | Takamura et al. |
| 2014/0038909 A1 | 2/2014 | Takamura et al. |
| 2014/0286888 A1 | 9/2014 | Nagai et al. |
| 2014/0329914 A1 | 11/2014 | Kobayashi et al. |
| 2015/0105336 A1 | 4/2015 | Takamura et al. |
| 2015/0197359 A1 | 7/2015 | Nohara et al. |
| 2015/0258166 A1 | 9/2015 | Spirio et al. |
| 2015/0328279 A1 | 11/2015 | Ellis-Behnke et al. |
| 2016/0000966 A1 | 1/2016 | Kobayashi et al. |
| 2016/0015855 A1 | 1/2016 | Nohara et al. |
| 2016/0030628 A1 | 2/2016 | Kobayashi |
| 2016/0213906 A1 | 7/2016 | Horita et al. |
| 2016/0287744 A1 | 10/2016 | Kobayashi et al. |
| 2016/0317607 A1 | 11/2016 | Spirio et al. |
| 2016/0362451 A1 | 12/2016 | Gil et al. |
| 2017/0072008 A1 | 3/2017 | Mehta et al. |
| 2017/0128622 A1 | 5/2017 | Spirio et al. |
| 2017/0173105 A1 | 6/2017 | Mehta et al. |
| 2017/0173221 A1 | 6/2017 | Mehta et al. |
| 2017/0202986 A1 | 7/2017 | Gil et al. |
| 2018/0369452 A1 | 12/2018 | Maki et al. |
| 2019/0111165 A1 | 4/2019 | Gil et al. |

FOREIGN PATENT DOCUMENTS

| | | | |
|---|---|---|---|
| CN | 101198350 A | 6/2008 | |
| CN | 101378773 A | 3/2009 | |
| CN | 101514225 A | 8/2009 | |
| EP | 2146667 A2 | 1/2010 | |
| EP | 2345433 A1 | 7/2011 | |
| EP | 2823830 A1 | 1/2015 | |
| EP | 3031466 A1 | 6/2016 | |
| JP | 2005-515796 A | 6/2005 | |
| JP | 2005-263631 A | 9/2005 | |
| JP | 2007-105186 A | 4/2007 | |
| JP | 2007-526232 A | 9/2007 | |
| JP | 2008-505919 A | 2/2008 | |
| JP | 2008-539257 A | 11/2008 | |
| JP | 2008-546689 A | 12/2008 | |
| JP | 2009-011341 A | 1/2009 | |
| JP | 2009-535338 A | 10/2009 | |
| JP | 2010-280719 A | 12/2010 | |
| JP | 2012-082180 A | 4/2012 | |
| JP | 5255274 B2 | 8/2013 | |
| JP | 2014-527543 A | 10/2014 | |
| JP | 5730828 B2 | 6/2015 | |
| JP | 5922749 B2 | 5/2016 | |
| WO | WO 94/17811 * | 8/1994 | ............. A61K 33/18 |
| WO | WO-1996/040033 A1 | 12/1996 | |
| WO | WO-1997/037694 A1 | 10/1997 | |
| WO | WO-99/53019 A1 | 10/1999 | |
| WO | WO-00/01238 A1 | 1/2000 | |
| WO | WO-2002/022072 A2 | 3/2002 | |
| WO | WO-02/062969 A2 | 8/2002 | |
| WO | WO-2002/058749 A2 | 8/2002 | |
| WO | WO-2002/062961 A2 | 8/2002 | |
| WO | WO-03/084980 A2 | 10/2003 | |
| WO | WO-03/096972 A2 | 11/2003 | |
| WO | WO-2004/007532 A2 | 1/2004 | |
| WO | WO-2005/001076 A2 | 1/2005 | |
| WO | WO-2005/014615 A2 | 2/2005 | |
| WO | WO-2005/082399 A2 | 9/2005 | |
| WO | WO 2006/014570 A2 | 2/2006 | |
| WO | WO 2006/116524 A1 | 11/2006 | |
| WO | WO-2006/138023 A1 | 12/2006 | |
| WO | WO-2007/076032 A2 | 7/2007 | |
| WO | WO-2007/142757 A2 | 12/2007 | |
| WO | WO 2008/039483 A2 | 4/2008 | |
| WO | WO-2008/073392 A2 | 6/2008 | |
| WO | WO-2008/073395 A2 | 6/2008 | |
| WO | WO-2008/113030 A2 | 9/2008 | |
| WO | WO-2008/127607 A2 | 10/2008 | |
| WO | WO 2008/134544 A1 | 11/2008 | |
| WO | WO-2009/072556 A1 | 6/2009 | |
| WO | WO-2010/041636 A1 | 4/2010 | |
| WO | WO-2012/008967 A1 | 1/2012 | |
| WO | WO-2013/030673 A2 | 3/2013 | |
| WO | WO-2013/133413 A1 | 9/2013 | |
| WO | WO-2014/008400 A2 | 1/2014 | |
| WO | WO-2014/076660 A1 | 5/2014 | |
| WO | WO-2014/136081 A1 | 9/2014 | |
| WO | WO-2014/141143 A1 | 9/2014 | |
| WO | WO-2014/141160 A1 | 9/2014 | |
| WO | WO-2015/027203 A1 | 2/2015 | |
| WO | WO-2015/030063 A1 | 3/2015 | |
| WO | WO-2015/136370 A2 | 9/2015 | |
| WO | WO-2015/138473 A1 | 9/2015 | |
| WO | WO-2015/138475 A1 | 9/2015 | |
| WO | WO-2015/138478 A1 | 9/2015 | |
| WO | WO-2015/138514 A1 | 9/2015 | |
| WO | WO-2017/120092 A1 | 7/2017 | |

OTHER PUBLICATIONS

Extended European Search Report issued in European Patent Application No. 09819170.3 dated Nov. 27, 2013.

Japanese Office Action dated Sep. 2, 2014, issued in Japanese Application No. 2010-532910, together with an English translation thereof.

Author Not Known, Medical Devices: Guidance Document, Borderline products, drug-delivery products and medical devices incorporating, as an integral part, an ancillary medicinal substance or an ancillary human blood derivative, European Commission, DG Enterprise and Industry, Directorate F, Unit F3 "Cosmetics and medical devices", 22 pages (Dec. 3, 2009) <http://ec.europa.eu/health/medical-devices/files/meddev/2_1_3_rev_3-12_2009_en.pdf> [last accessed on May 4, 2015].

Written Opinion for PCT/JP2009/067367, 5 pages (dated Dec. 15, 2009).

Gherli, T. et al., Comparing warfarin with aspirin after biological aortic valve replacement: a prospective study, Circulation, 110(5):496-500 (2004).

Caplan, M.R. et al., Control of self-assembling oligopeptide matrix formation through systematic variation of amino acid sequence, Biomaterials, 23(1):219-27 (2002).

Caplan, M.R. et al., Effects of systematic variation of amino acid sequence on the mechanical properties of a self-assembling, oligopeptide biomaterial, J. Biomater. Sci. Polymer Edn., 13(3):225-236 (2002).

Caplan, M.R. et al., Self-assembly of a beta-sheet protein governed by relief of electrostatic repulsion relative to van der Waals attraction, Biomacromolecules, 1(4):627-31 (2000).

Gelain, F. et al., Designer self-assembling peptide scaffolds for 3-d tissue cell cultures and regenerative medicine, Macromol. Biosci., 7(5):544-51 (2007).

Hwang, W. et al., Supramolecular structure of helical ribbons self-assembled from a beta-sheet peptide, The Journal of Chemical Physics, 118(1): 389-397 (2003).

Kisiday, J. et al., Self-assembling peptide hydrogel fosters chondrocyte extracellular matrix production and cell division: implications for cartilage tissue repair, Proc. Natl. Acad. Sci. U S A, 99(15):9996-10001 (2002).

Kumada, Y. et al., Functionalized scaffolds of shorter self-assembling peptides containing MMP-2 cleavable motif promote fibroblast proliferation and significantly accelerate 3-D cell migration independent of scaffold stiffness, Soft Matter, The Royal Society of Chemistry, 7 pages (2010).

(56) References Cited

OTHER PUBLICATIONS

Leon, E.J. et al., Mechanical properties of a self-assembling oligopeptide matrix, J. Biomater. Sci. Polymer Edn., 9(3):297-312 (1998).
Luo, Z. and Zhang, S., Designer nanomaterials using chiral self-assembling peptide systems and their emerging benefit for society, Chem. Soc. Rev., 41(13):4736-54 (2012).
Marini, D.M. et al., Left-Handed Helical Ribbon Intermediates in the Self-Assembly of a beta-Sheet Peptide, Nano Letters, 2(4):295-299 (2002).
Yokoi, H. et al., Dynamic reassembly of peptide RADA16 nanofiber scaffold, Proc. Natl. Acad. Sci. U S A, 102(24):8414-9 (2005).
Zhang, S. et al., Building from the bottom up, Materials Today, 20-27 (2003).
Zhang, S. Self-assembling peptide materials, Amino Acids, Pept. Proteins, 37:40-65 (2012).
Zhang, S., Beyond the Petri dish, Nat. Biotechnol., 22(2):151-2 (2004).
Zhang, S., Designer Self Assembling Peptide Nanofiber Scaffolds for Study of 3 D Cell Biology and Beyond, Cancer Research, 335-362 (2008).
Zhang, S., Emerging biological materials through molecular self-assembly, Biotechnol. Adv., 20(5-6):321-39 (2002).
Zhang, S., Fabrication of novel biomaterials through molecular self-assembly, Nat. Biotechnol., 21(10):1171-8 (2003).
Zhaoyang, Y. et al., Temperature and pH effects on biophysical and morphological properties of self-assembling peptide RADA16-I, Journal of Peptide Science, 14(2):152-162 (2008).
U.S. Appl. No. 14/046,386 (Tissue Occluding Agent Comprising an IEIKIEIKIEIKI Peptide, filed Feb. 6, 2014), Claims as filed Feb. 12, 2016.
Declaration of Satoru Kobayashi, MSc and Kyoji Hirai, MD, PhD for U.S. Appl. No. 14/239,954, 5 pages (May 2017).
Beam, J., Wound Cleansing: Water or Saline?, Journal of Athletic Training, 41(2): 196-197 (2006).
Chen, P., Self-assembly of ionic-complementary peptides: a physicochemical viewpoint, Colloids and Surfaces A: Physicochemical and Engineering Aspects, 261(1-3): 3-24 (2005).
Concaro, S. et al, Effect of different materials on the proliferation and migration of articular chondrocytes, Osteoarthritis and Cartilage, 15:Supplement B, pp. B119 (2007).
Davis, M.E. et al, Custom design of the cardiac microenvironment with biomaterials, Circ Res., 97(1):8-15 (2005).
Davis, M.E. et al, Local myocardial insulin-like growth factor 1 (IGF-1) delivery with biotinylated peptide nanofibers improves cell therapy for myocardial infarction, Proc. Natl. Acad. Sci. USA. ,103(21):8155-8160 (2006).
Davis, M.E. et al., Injectable self-assembling peptide nanofibers create intramyocardial microenvironments for endothelial cells, Circulation, 111(4):442-50 (2005).
Ellis-Behnke, R.G. et al, Nano neuro knitting: peptide nanofiber scaffold for brain repair and axon regeneration with functional return of vision, Proc. Natl. Acad. Sci. USA, 103(13):5054-5059 (2006).
Ellis-Behnke, R.G. et al., Nano hemostat solution: immediate hemostasis at the nanoscale, Nanomedicine, 2(4):207-15 (2006).
Garreta, E. et al, Osteogenic differentiation of mouse embryonic stem cells and mouse embryonic fibroblasts in a three-dimensional self-assembling peptide scaffold, Tissue Eng., 12(8):2215-27 (2006).
Guo, J. et al, Reknitting the injured spinal cord by self-assembling peptide nanofiber scaffold, Nanomedicine, 3(4):311-321 (2007).
Horii, A. et al, Biological designer self-assembling peptide nanofiber scaffolds significantly enhance osteoblast proliferation, differentiation and 3-D migration, PLoS One, 2(2):e190 (2007).
Hsieh, P.C. et al, Controlled delivery of PDGF-BB for myocardial protection using injectable self-assembling peptide nanofibers, J. Clin. Invest.,116(1):237-248 (2006).
Hsieh, P.C.H. et al, Local controlled intramyocardial delivery of platelet-derived growth factor improves postinfarction ventricular function without pulmonary toxicity, Circulation, 114(7):637-644 (2006).
Kohgo, T. et al, Poster 110: Bone Regeneration for Dental Implants Using Tissue-Engineered Bone With Self-Assembling Peptide Nanofiber 3-Dimensional (3D) Scaffolds, Journal of Oral and Maxillofacial Surgery, 65(9): Supplement, p. 43.e63 (2007).
Misawa, H. et al, PuraMatrix facilitates bone regeneration in bone defects of calvaria in mice, Cell Transplant, 15(10):903-910 (2006).
Narmoneva, D.A. et al, Endothelial cells promote cardiac myocyte survival and spatial reorganization: implications for cardiac regeneration, Circulation, 110(8):962-968 (2004).
Nichol, J.W. et al, Co-culture induces alignment in engineered cardiac constructs via MMP-2 expression, Biochem. Biophys. Res. Commun., 373(3):360-365 (2008).
Segers, V.F. And Lee, R.T., Local delivery of proteins and the use of self-assembling peptides, Drug Discov. Today, 12(13-14):561-8 (2007).
Segers, V.F.M. And Lee, R.T., Stem-cell therapy for cardiac disease, Nature 451, 937-942 (2008).
Segers, V.F.M. et al, Local delivery of protease-resistant stromal cell derived factor-1 for stem cell recruitment after myocardial infarction, Circulation, 116(15):1683-1692 (2007).
Semino, C.E., Self-assembling peptides: from bio-inspired materials to bone regeneration, J. Dent Res., 87(7):606-616 (2008).
Serban, M.A. et al, Effects of extracellular matrix analogues on primary human fibroblast behavior, Acta Biomater., 4(1):67-75 (2008).
Shivachar, A.C., Isolation and Culturing of Glial, Neuronal and Neural Stem Cell Types Encapsulated in Biodegradable Peptide Hydrogel, Topics in Tissue Engineering, vol. 4. Eds. N. Ashammakhi, R Reis, & F Chiellini © 2008.
Spencer, N.J. et al, Peptide- and collagen-based hydrogel substrates for in vitro culture of chick cochleae, Biomaterials, 29(8):1028-1042 (2008).
Thonhoff, J.R. et al, Compatibility of human fetal neural stem cells with hydrogel biomaterials in vitro, Brain Res., 1187:42-51 (2008).
Tokunou, T. et al, Engineering insulin-like growth factor-1 for local delivery, Faseb J., 22(6):1886-1893 (2008).
Van Putten, S.M. et al, the downmodulation of the foreign body reaction by cytomegalovirus encoded interleukin-10, Biomaterials, 30(5):730-735 (2008).
Yamaoka, H. et al, Cartilage tissue engineering using human auricular chondrocytes embedded in different hydrogel materials, J. Biomed. Mater Res. A., 78(1):1-11 (2006).
Osterman, D. G. And Kaiser, E.T., Design and Characterization of Peptides With Amphiphilic β-Strand Structures, Journals of Cellular Biochemistry, 29: 57-72 (1985).
Akers, M. J., Chapter 26: Parenteral Preparations, Remington: Essentials of Pharmaceutics, Edited by Linda Felton, Pharmaceutical Press, p. 497 (2012).
Arista ™ Information Sheet, Medafor, Inc., 6 pages (2006).
CoSeal® Surgical Sealant, Information Sheet, Baxter Healthcare Corporation, 8 pages (2006).
Reich, I. et al., Chapter 36: Tonicity, Osmoticity, Osmolality, and Osmolarity, Remington: Practice of the Science and Pharmacy, 19th edition, Mack Publishing Company, 613-621 (1995).
Yamamoto, H. et al, A novel method of endoscopic mucosal resection using sodium hyaluronate, Gastrointestinal Endoscopy, 50(2): 251-256 (1999). [Abstract].
3-D Matrix Japan, Ltd. Company Profile Power Point, 32 pages, May 2005 (with English translation).
3D-Matrix Japan, Products, FAQs, 8 pages, dispatched Sep. 20, 2011 [English translation].
[No Author Listed] Fluid. Iwanami Rikagaku Dictionary, 3rd edition Incremental version, 2nd Print, Oct. 20, 1981, p. 1430, Partial English Translation, 1 Page.
Abukawa, H. et al, Reconstructing Mandibular Defects Using Autologous Tissue-Engineered Tooth and Bone Constructs, J. Oral Maxillofac. Surg., 67(2):335-347 (2009).
Allen, P. et al, Type I collagen, fibrin and PuraMatrix matrices provide permissive environments for human endothelial and mesenchymal progenitor cells to form neovascular networks, J. Tissue Eng. Regen Med., 5(4):e74-86 (2011).
Altman, M. et al., Conformational behavior of ionic self-complementary peptides, Protein Sci., 9(6):1095-105 (2000).

(56) References Cited

OTHER PUBLICATIONS

Anderson, I. The properties of hyaluronan and its role in wound healing, Prof. Nurse., 17(4):232-5 (2001).
Arosio, P. et al, End-to-end self-assembly of RADA 16-I nanofibrils in aqueous solutions, Biophys. J., 102(7): 1617-26 (2012).
Author Unknown, Acrodisc® Syringe Filter with Supor® Membrane -0.2 µl3mm (1000/pkg), Product ID: 4692, Pall Shop, accessed from <<https://shop.pall.com/us/en/laboratory/sterile-filtration-and-clarification/mycoplasma-reduction/acrodisc-syringe-filters-with-supor-membrane-zid4692>> (2019).
Author Unknown, AORNs Recommended Practices for Maintaining a Sterile Field is Up for Review and Public Comment Through Mar. 25, 2005, retrieved from <<https://www.infectioncontroltoday.com/guidelines/aorns-recommended-practices-maintaining-sterile-field-review-and-public-comment-through>>, accessed on Dec. 19, 2018 (23 pages).
Basford, P.J., et al., Endoscopic resection of sporadic duodenal adenomas: comparison of endoscopic mucosal resection (EMR) with hybrid endoscopic submucosal dissection (ESD) techniques and the risks of late delayed bleeding, Surg. Endosc., 28: 1594-1600 (2014).
Baumfalk and Finazzo, Filter Integrity testing helps to ensure that GMP sterility requirements are met, BioPharm International, 19(6): 1-3 (2006).
BD PuraMatrix Peptide Hydrogel, Catalog No. 354250, BD Biosciences, 1-16 (2004).
BD PuraMatrix Peptide Hydrogel, Product Specification Sheet, 1 page (2004).
Becton, Dickinson and Company, Positively Unique: BD PosiFlush™ Pre-Filled Syringes, Brochure, 6 pages (Jun. 2010).
Bouten, C.V. et al, Substrates for cardiovascular tissue engineering, Adv. Drug Deliv. Rev., 63(4-5):221-41 (2011).
Boyle, A. L., Applications of de novo designed peptides, Peptide Applications in Biomedicine, Biotechnology and Bioengineering, 51-86 (2017).
Branco, M.C. And Schneider, J.P., Self-assembling materials for therapeutic delivery, Acta. Biomaterialia, 5(3): 817-831 (2009).
Cai, L. et al, Injectable Hydrogels with in Situ Double Network Formation Enhance Retention of Transplanted Stem Cells, Adv. Funct. Mater., 1-8 (2015).
Censi, R. et al, Hydrogels for protein delivery in tissue engineering, J. Control Release, 161(2):680-692 (2012).
Chambers, J. et al, Memorandum regarding Nucleic Acid and Peptide Claim Interpretation: "A" and "The," USPTO, 2 pages, Dec. 29, 2005.
Chen, K. et al, A Hybrid Silk/RADA-Based Fibrous Scaffold with Triple Hierarchy for Ligament Regeneration, Tissue Eng. Part A., 18(13-14):1399-409 (2012).
Cigognini, D. et al, Evaluation of early and late effects into the acute spinal cord injury of an injectable functionalized self-assembling scaffold, PLoS One., 6(5): e19782 (2011).
Cooper et al., Testing the "critical-size" in calvarial bone defects: revisiting the concept of a critical-sized defect (CSD), Plast Reconstr Surg. 125(6): 1685-1692, 2010.
Cryolife®, Life Restoring Technologies, BioGlue® Instructions for Use: Surgical Adhesive Syringe Instructions for Use, L6312.008-(Apr. 2014), pp. 1-15, 16 pages (2014).
Cunha, C. et al, Emerging nanotechnology approaches in tissue engineering for peripheral nerve regeneration, Nanomedicine, 7(1):50-59 (2011).
Cunha, C. et al., 3D culture of adult mouse neural stem cells within functionalized self-assembling peptide scaffolds, International Journal of Nanomedicine, 943-955 (2011).
Curley, J.L. et al, Fabrication of micropatterned hydrogels for neural culture systems using dynamic mask projection photolithography, J. Vis. Exp., 48: 2636 (2011).
Decision of the Opposition Division in EP Application No. EP2345433, 36 pages, dated Jul. 8, 2019.

Driscoll, P., What are the differences and similarities between laparoscopy and endoscopy?, 1 page (2016), <https//www.quora.com/what-are-the-differences-and-similiarities-between-laparoscopy-and-endoscopy> Retrieved on Oct. 4, 2017.
Dutta, R.C. And Dutta, A.K., Comprehension of ECM-Cell dynamics: A prerequisite for tissue regeneration, Biotechnol. Adv., 28(6):764-769 (2010).
Dégano, I.R. et al, the effect of self-assembling peptide nanofiber scaffolds on mouse embryonic fibroblast implantation and proliferation, Biomaterials, 30(6):1156-65 (2009).
Eisenbud, D. et al, Hydrogel Wound Dressings: Where Do We Stand in 2003?, Ostomy Wound Manage, 49(10): 52-57 (2003).
Ellis-Behnke, R. et al, Crystal clear surgery with self-assembling molecules that act as a barrier in the brain and intestine, Abstracts / Nanomedicine: Nanotechnology, Biology, and Medicine, 1:269-270 (2005).
Ellis-Behnke, R., At the nanoscale: nanohemostat, a new class of hemostatic agent, WIREs Nanomedicine and Nanobiotechnology, 3: 70-78 (2011).
Gelain, F. et al., Slow and sustained release of active cytokines from self-assembling peptide scaffolds, Journal of Controlled Release, 145:231-239 (2010).
Gervaso, F. et al, the biomaterialist's task: scaffold biomaterials and fabrication technologies, Joints 1(3): 130-137 (2013).
Ginsberg, M., Good Medicine/Bad Medicine and the Law of Evidence: Is There a Role for Proof of Character, Propensity, or Prior Bad Conduct in Medical Negligence Litigation?, South Caroline Law Review, 63:367-402 (2011).
Giri, S. And Bader, A., Improved preclinical safety assessment using micro-BAL devices: the potential impact on human discovery and drug attrition, Drug Discov. Today, 16(9-10):382-397 (2011).
Gonzales, A.L. et al., Integrin interactions with immobilized peptides in polyethylene glycol diacrylate hydrogels, Tissue Eng., 10(11-12):1775-86 (2004).
Guo, H.D. et al, Sustained delivery of VEGF from designer self-assembling peptides improves cardiac function after myocardial infarction, Biochem. Biophys. Res. Commun., 424(1):105- 111 (2012).
Guo, H.D. et al, Transplantation of marrow-derived cardiac stem cells carried in designer self-assembling peptide nanofibers improves cardiac function after myocardial infarction, Biochem. Biophys. Res. Commun., 399(1):42-48 (2010).
Gurski, L.A. et al, 3D Matrices for Anti-Cancer Drug Testing and Development, Oncology, Issues Jan./Feb. 2010: 20-25.
Hartgerink, J.D. et al., Peptide-amphiphile nanofibers: a versatile scaffold for the preparation of self-assembling materials, Proc. Natl. Acad. Sci. U S A., 99(8):5133-8 (2002).
Hemmrich, K. et al., Implantation of preadipocyte-loaded hyaluronic acid-based scaffolds into nude mice to evaluate potential for soft tissue engineering, Biomaterials, 26(34):7025-37 (2005).
Henriksson, H. et al, Investigation of different cell types and gel carriers for cell-based intervertebral disc therapy, in vitro and in vivo studies, J. Tissue Eng. Regen. Med., doi: 10.1002/term.480 (2011).
Henriksson, H.B. et al, Transplantation of human mesenchymal stems cells into intervertebral discs in a xenogeneic porcine model, Spine (Phila Pa 1976), 34(2):141-148 (2009).
Hilton, J. R. et al, Wound Dressings in Diabetic Foot Disease, Clinical Infectious Diseases, 39: S100-3 (2004).
Hirai, K. et al, the fundamental study of Matrigel (PuraMatrix TM) for the hemostasis of bleeding from pulmonary artery and vein or the prevention of lung fistel, Gen Thorac Cardiovasc Surg, 59 (Supplement): 600 (2011).
Hollinger, J.O. And Kleinschmidt, J.C., "The critical size defect as an experimental model to test bone repair materials," J. Craniofac Surg 1990(1): 60-68.
Holmes, T.C. et al., Extensive neurite outgrowth and active synapse formation on self-assembling peptide scaffolds, Proc. Natl. Acad. Sci. U S A., 97(12):6728-33 (2000).
Huang, A.H. et al, Mechanics and mechanobiology of mesenchymal stem cell-based engineered cartilage, J. Biomech., 43(1):128-136 (2010).

(56) References Cited

OTHER PUBLICATIONS

Ingenito, E. P. et al, Bronchoscopic Lung Volume Reduction in Severe Emphysema, Proc. Am. Thorac Soc., 5(4): 454-460 (2008).
InjectorForce Max™, Olympus, Brochure, 3 pages (2012).
Kim, J.H. et al, the enhancement of mature vessel formation and cardiac function in infarcted hearts using dual growth factor delivery with self-assembling peptides, Biomaterials, 32(26):6080-6088 (2011).
Koh, R., et al. Antithrombotic drugs are risk factors for delayed postoperative bleeding after endoscopic submucosal dissection for gastric neoplasms, Gastrointest. Endosc., 78: 476-483 (2013).
Komatsu, S. et al,The Neutral Self-Assembling Peptide Hydrogel SPG-178 as a Topical Hemostatic Agent, PLoS ONE, 9(7): e102778 (2014).
Kopecek, J. And Yang, J., Peptide-directed self-assembly of hydrogels, Acta Biomaterialia, 5(3): 805-816 (2009).
Kubba, A.K. And Palmer, K. R., Role of endoscopic injection therapy in the treatment of bleeding peptic ulcer, British Journal of Surgery, 83: 461-468 (1996).
Kumada, Y. And Zhang, S., Significant type I and type III collagen production from human periodontal ligament fibroblasts in 3D peptide scaffolds without extra growth factors, PLoS One, 5(4):e10305 (2010).
Kyle, S. et al, Recombinant self-assembling peptides as biomaterials for tissue engineering, Biomaterials, 31: 9395-9405 (2010).
Kyle, S. et al., Production of self-assembling biomaterials for tissue engineering, Trends Biotechnol., 27(7):423-33 (2009).
Lampe, K.J. And Heilshorn, S.C., Building stem cell niches from the molecule up through engineered peptide materials, Neurosci. Lett., 519(2):138-46 (2012).
Leung, G.K. et al, Peptide nanofiber scaffold for brain tissue reconstruction, Methods Enzymol., 508:177-190 (2012).
Li, X. et al, Engineering neural stem cell fates with hydrogel design for central nervous system regeneration, Progress in Polymer Science, 37(8):1105-1129 (2012).
Liedmann, A. et al, Cultivation of human neural progenitor cells in a 3-dimensional self-assembling peptide hydrogel, J. Vis. Exp., (59):e3830 (2012).
Lin, H-J. et al, A prospective, randomized trial of large-versus small-volume endoscopic injection of epinephrine for peptic ulcer bleeding, Gastrointestinal Endoscopy, 55(6): 615-619 (2002).
Liu, J. et al., Controlled release of paclitaxel from a self-assembling peptide hydrogel formed in situ and antitumor study in vitro, International Journal of Nanomedicine, 6:2143-2153 (2011).
Liu, W-M. et al., Diversification of Microfluidic Chip for Applications in Cell-Based Bioanalysis, Chinese Journal of Analytical Chemistry, 40(1): 24-31 (2012).
Loo, Y. et al., From short peptides to nanofibers to macromolecular assemblies in biomedicine, Biotechnol. Adv., 30(3):593-603 (2012).
Louie, M. K. et al, Bovine Serum Albumin Glutaraldehyde for Completely Sutureless Laparoscopic Heminephrectomy in a Survival Porcine Model, Journal of Endourology, 24(3): 451-455 (2010).
Luo, Z. et al, Fabrication of self-assembling d-form peptide nanofiber scaffold d-EAK16 for rapid hemostasis, Biomaterials, 32(8):2013-20 (2011).
Lépilliez, V., et al., Endoscopic resection of sporadic duodenal adenomas: an efficient technique with a substantial risk of delayed bleeding, Endoscopy, 40: 806-810 (2008).
Maher, S.A. et al, A nano-fibrous cell-seeded hydrogel promotes integration in a cartilage gap model, J. Tissue Eng. Regen. Med., 4(1):25-29 (2010).
Marston, W.A. et al., Initial report of the use of an injectable porcine collagen-derived matrix to stimulate healing of diabetic foot wounds in humans, Wound Repair Regen., 13(3):243-7 (2005).
Masuhara, H. et al, Novel infectious agent-free hemostatic material (TDM-621) in cardiovascular surgery, Ann. Thorac. Cardiovasc. Surg. Methods Enzymol., 18(5):444-451 (2012).
McFadden, P. M., Minimally Invasive Thoracic Surgery, vol. 2, No. 3, Jul. 2000, pp. 137-144.
McGrath, A.M. et al, BD© PuraMatrix® peptide hydrogel seeded with Schwann cells for peripheral nerve regeneration, Brain Res. Bull., 83(5):207-213 (2010).
Meng, H. et al, Peripferal Nerve Regeneration in Response to Synthesized Nanofiber Scaffold Hydrogel, Life Science Journal, 9(1): 42-46 (2012).
Mimotopes, A Guide to Handling and Storing Peptides, PU3-004-1, Feb. 20, 2011, Date established via internet achieve http://www.mimotopes.com/files/editor upload/File/PeptidesAndAntibodies/PU3004-1Handling-and-Storing-Peptides.PDF.
Mooney, M.P. And Siegel, M.I., Animal models for bone tissue engineering of critical-sized defects (CSDs), bone pathologies, and orthopedic disease states, In: Hollinger, JO.; Einhorn, TA.; Doll, BA.; Sfeir, C. Editors. Bone Tissue Engineering. Boca Raton, FL: C.R.C. Press, pp. 217-244 (2005).
Moser, C. et al, Autologous fibrin sealant reduces the incidence of prolonged air leak and duration of the chest tube drainage after lung volume reduction surgery: a prospective randomized blinded study, Journal of Thoracic and Cardiovascular Surgery, 136(4): 843-849 (2008).
Nakahara, H. et al, Bone repair using a hybrid scaffold of self-assembling peptide PuraMatrix and polyetheretherketone cage in rats, Cell Transplant, 19(6):791-797 (2010).
Narmoneva, D.A. et al., Self-assembling short oligopeptides and the promotion of angiogenesis, Biomaterials, 26(23):4837-46 (2005).
Nishimura, A. et al., Controlled release of insulin from self-assembling nanofiber hydrogel, PuraMatrix: application for the subcutaneous injection in rats, European Journal of Pharmaceutical Sciences, 45:1-7 (2012).
Olson, E. J., Hyperinflated Lungs: What does it mean?, A recent chest X-ray showed that I have hyperinflated lungs. What could cause this?, Mayo Clinic, Nov. 30, 2017, retrieved from <<https://www.mayoclinic.org/diseases-conditions/emphysema/expert-answers/hyperinflated-lungs/faq-20058169>>, 3 pages, accessed Feb. 14, 2019.
Ono, S. et al., Thienopyridine derivatives as risk factors for bleeding following high risk endoscopic treatments: Safe Treatment on Antiplatelets (STRAP) study, Endoscopy, 47: 632-637 (2015).
Ortinau, S. et al, Effect of 3D-scaffold formation on differentiation and survival in human neural progenitor cells, Biomed. Eng. Online, 9(1):70 (2010).
Paramasivam, E., Air leaks, pneumothorax, and chest drains, Continuing Education in Anesthesia, Critical Care & Pain, vol. 8 No. 6 2008.
Patterson, J. et al., Biomimetic materials in tissue engineering, Materials today, 13(1-2): 14-22 (2010).
Pioche, M. et al, A self-assembling matrix-forming gel can be easily and safely applied to prevent delayed bleeding after endoscopic resections, Endoscopy International Open, 4: E415-E419 (2016).
Saiga, K. et al, Combined use of bFGF and GDF-5 enhances the healing of medial collateral ligament injury, Biochem. Biophys. Res. Commun., 402(2):329-334 (2010).
Sanborn, T.J. et al., A Thermally Triggered, Enzymatically Cross-linked PEG-Peptide Hydrogel for Biomaterial Applications, Presented at 2001 Annual Meeting, Americal Institute of Chemical Engineers, Reno, NV, Nov. 4-9, 2001.
Scalfani, a.p. And Romo III., T., Injectable fillers for facial soft tissue enhancement, Facial Plast. Surg., 16(1):29-34 (2000).
Semino, C.E. et al., Entrapment of migrating hippocampal neural cells in three-dimensional peptide nanofiber scaffold, Tissue Eng., 10(3-4):643-55 (2004).
Shirai, K. et al, Multipotency of clonal cells derived from swine periodontal ligament and differential regulation by fibroblast growth factor and bone morphogenetic protein, J. Periodontal Res., 44(2):238-247 (2009).
Song, H. et al, Hemostatic efficacy of biological self-assembling peptide nanofibers in a rat kidney model, Macromol Biosci., 10(1):33-39 (2010).
Spotnitz, W. D. And Banks, S., Hemostats, sealants and adhesives: components of the surgical toolbox, Transfusion, 48: 1502-1516 (2008).

(56) References Cited

OTHER PUBLICATIONS

Stark, J. and De Leval, M., Experience with fibrin seal (Tisseel) in operations for congenital heart defects, Ann. Thorac, Surg., 38(4):411-3 (1984).

Stiuso, P. et al., The self-association of protein SV-IV and its possible functional implications, Eur. J. Biochem., 266(3):1029-35 (1999).

Sur, S. et al, A hybrid nanofiber matrix to control the survival and maturation of brain neurons, Biomaterials, 33(2):545-55 (2012).

Takei, J., 3-Dimensional Cell Culture Scaffold for Everyone: Drug Screening, Tissue Engineering and Cancer Biology, AATEX, 11(3): 170-176 (2006).

Tam, J. et al., Fractional skin harvesting: autologous skin grafting without donor-site morbidity, Plastic and Reconstructive Surgery Global Open, 1(6): e47 (2013).

Thermo Scientific, MaxQ 2000 Open-Air Platform Shaker, 30 pages (2010).

Tokunaga, M. et al, Implantation of cardiac progenitor cells using self-assembling peptide improves cardiac function after myocardial infarction, J. Mol. Cell. Cardiol., 49(6):972-983 (2010).

Uemura, M. et al, Matrigel supports survival and neuronal differentiation of grafted embryonic stem cell-derived neural precursor cells, J. Neurosci. Res., 88(3):542-551 (2010).

Wang, Q.G. et al, the composition of hydrogels for cartilage tissue engineering can influence glycosaminoglycan profile, Eur. Cell Mater, 19:86-95 (2010).

Wang. T. et al, Molecular Mechanisms of RAD16-1 Peptide on Fast Stop Bleeding in Rat Models, Int. J. Mol. Sci., 13: 15279-15290 (2012).

Week 201413 Thomson Scientific, London, GB; AN 2013-U98585, XP0027 40500, Use of nigella glandulifera freyn 3 seed grass volatile oil for preparing medicine for treating chronic obstructive pulmonary disease, & CN 103 251 690 A People'S Liberation Army Xinjiang Milita) Aug. 21, 2013 (Aug. 21, 2013) abstract.

Whatman Product Guide, 2 pages (1997).

Wu, M. et al., Self-assembling peptide nanofibrous hydrogel on immediate hemostasis and accelerative osteosis, Biomacromolecules, 16: 3112-3118 (2015).

Wu, X. et al, Functional self-assembling peptide nanofiber hydrogel for peripheral nerve regeneration, Regenerative Biomaterials, 21-30 (2016).

Yla-Outinen, L. et al, Three-dimensional growth matrix for human embryonic stem cell-derived neuronal cells, J. Tissue Eng. Regen. Med., doi: 10.1002/term.1512 (2012).

Yoshida, M, et al., Initial clinical trial of a novel hemostat, TDM-621, in the endoscopic treatments of the gastric tumors, J. Gastroenterol Hepatol., 29: 77-79 (2014).

Yoshimi, R. et al, Self-assembling peptide nanofiber scaffolds, platelet-rich plasma, and mesenchymal stem cells for injectable bone regeneration with tissue engineering, J. Craniofac. Surg., 20(5):1523-1530 (2009).

Yu, Y.C. et al., Construction of biologically active protein molecular architecture using self-assembling peptide-amphiphiles, Methods Enzymol., 289:571-87 (1997).

Zarzhitsky, S. and Rapaport, H., The interactions between doxorubicin and amphiphilic and acidic ß-sheet peptides towards drug delivery hydrogels, J. Colloid Interface Sci. 360(2):525-531 (2011).

Zhang, S. et al, PuraMatrix: Self-Assembling Peptide Nanofiber Scaffolds, Scaffolding in Tissue Engineering, Chapter 15, 217-238 (1992).

Zhang, S. et al, Self-assembling peptides in biology, materials science and engineering, Peptide Science—Present and Future, 737-744 (1999).

Zhang, S. et al, Self-complementary oligopeptide matrices support mammalian cell attachment, Biomaterials, 16(18): 1385-1393 (1995).

Zhang, S., Hydrogels: Wet or let die, Nat. Mater., 3(1):7-8 (2004).

Zhao, X. et al., Recent development of peptide self-assembly, Progress in Natural Science 18, 6(10):653-660 (2008).

Zhou, X-R. et al., Self-assembly of PH and calcium dual-responsive peptide-amphiphilic hydrogel, Journal of Peptide Science, 19: 737-744 (2013).

"International Search Report, dated Dec. 15, 2009, issued in PCT/JP2009/067367".

Ye et al., "Temperature and PH effects on biophysical and morphological properties of self-assembling peptide RADA16-I", Journal of Peptide Science, Jan. 14, 2008, vol. 14, No. 2, pp. 152-162.

PuraStat® Synthetic Surgical Hemostatic Agent, Product Information, Nanotechnology Products Database, registration date Mar. 30, 2017, retrieved from <https://product.statnano.com/product/8558>, accessed on Oct. 11, 2019.

\* cited by examiner a)

b)

c)

d)

a)

b)

SEQUENCE LISTING

```
<160> NUMBER OF SEQ ID NOS: 11

<210> SEQ ID NO 1
<211> LENGTH: 16
<212> TYPE: PRT
<213> ORGANISM: Artificial
<220> FEATURE:
<223> OTHER INFORMATION: designed peptide
<220> FEATURE:
<221> NAME/KEY: MOD_RES
<222> LOCATION: (1) .. (1)
<223> OTHER INFORMATION: ACETYLATION
```

```
<400> SEQUENCE: 1

Arg Ala Asp Ala Arg Ala Asp Ala Arg Ala Asp Ala Arg Ala Asp Ala
1               5                   10                  15

<210> SEQ ID NO 2
<211> LENGTH: 13
<212> TYPE: PRT
<213> ORGANISM: Artificial
<220> FEATURE:
<223> OTHER INFORMATION: designed peptide
<220> FEATURE:
<221> NAME/KEY: MOD_RES
<222> LOCATION: (1)..(1)
<223> OTHER INFORMATION: ACETYLATION

<400> SEQUENCE: 2

Ile Glu Ile Lys Ile Glu Ile Lys Ile Glu Ile Lys Ile
1               5                   10

<210> SEQ ID NO 3
<211> LENGTH: 12
<212> TYPE: PRT
<213> ORGANISM: Artificial
<220> FEATURE:
<223> OTHER INFORMATION: designed peptide
<220> FEATURE:
<221> NAME/KEY: MOD_RES
<222> LOCATION: (1)..(1)
<223> OTHER INFORMATION: ACETYLATION

<400> SEQUENCE: 3

Lys Leu Asp Leu Lys Leu Asp Leu Lys Leu Asp Leu
1               5                   10

<210> SEQ ID NO 4
<211> LENGTH: 9
<212> TYPE: PRT
<213> ORGANISM: Artificial
<220> FEATURE:
<223> OTHER INFORMATION: designed peptide
<220> FEATURE:
<221> NAME/KEY: MOD_RES
<222> LOCATION: (1)..(1)
<223> OTHER INFORMATION: ACETYLATION

<400> SEQUENCE: 4

Ile Glu Ile Lys Ile Glu Ile Lys Ile
1               5

<210> SEQ ID NO 5
<211> LENGTH: 4
<212> TYPE: PRT
<213> ORGANISM: Artificial
<220> FEATURE:
<223> OTHER INFORMATION: designed peptide

<400> SEQUENCE: 5

Arg Ala Asp Ala
1

<210> SEQ ID NO 6
<211> LENGTH: 16
<212> TYPE: PRT
<213> ORGANISM: Artificial
<220> FEATURE:
<223> OTHER INFORMATION: designed peptide
```

```
<400> SEQUENCE: 6

Arg Ala Asp Ala Arg Ala Asp Ala Arg Ala Asp Ala Arg Ala Asp Ala
1               5                   10                  15

<210> SEQ ID NO 7
<211> LENGTH: 4
<212> TYPE: PRT
<213> ORGANISM: Artificial
<220> FEATURE:
<223> OTHER INFORMATION: designed peptide

<400> SEQUENCE: 7

Ile Glu Ile Lys
1

<210> SEQ ID NO 8
<211> LENGTH: 13
<212> TYPE: PRT
<213> ORGANISM: Artificial
<220> FEATURE:
<223> OTHER INFORMATION: designed peptide

<400> SEQUENCE: 8

Ile Glu Ile Lys Ile Glu Ile Lys Ile Glu Ile Lys Ile
1               5                   10

<210> SEQ ID NO 9
<211> LENGTH: 9
<212> TYPE: PRT
<213> ORGANISM: Artificial
<220> FEATURE:
<223> OTHER INFORMATION: designed peptide

<400> SEQUENCE: 9

Ile Glu Ile Lys Ile Glu Ile Lys Ile
1               5

<210> SEQ ID NO 10
<211> LENGTH: 4
<212> TYPE: PRT
<213> ORGANISM: Artificial
<220> FEATURE:
<223> OTHER INFORMATION: designed peptide

<400> SEQUENCE: 10

Lys Leu Asp Leu
1

<210> SEQ ID NO 11
<211> LENGTH: 12
<212> TYPE: PRT
<213> ORGANISM: Artificial
<220> FEATURE:
<223> OTHER INFORMATION: designed peptide

<400> SEQUENCE: 11

Lys Leu Asp Leu Lys Leu Asp Leu Lys Leu Asp Leu
1               5                   10
```

TISSUE OCCLUDING AGENT COMPRISING AN IEIKIEIKIEIKI PEPTIDE

TECHNICAL FIELD

The present invention relates to a tissue occluding agent comprising a self-assembling peptide hydrogel.

BACKGROUND ART

Tissue occlusion to prevent leakage of body fluids (blood, tissue fluids and the like) caused by tissue damage have major significance in clinical situations, including surgery. Effectively inhibiting body fluid leakage from damage sites is associated with improved life support during surgery and improved post-surgical quality of life (QOL).

Hemostasis is considered clinically important for the following reasons.

1. Blood loss is a major cause of death, with causes of blood loss including serious trauma, aneurysm, esophageal and gastric ulcers, and esophageal varix rupture. Probability of death is high when hemorrhage cannot be immediately arrested.

2. Hemorrhage during surgery is a major concern, since hemorrhage can lead to systemic infection or organ dysfunction. Hemorrhage not only interferes with the object of surgery, but removal of hemorrhaged blood is also a delaying factor in surgery.

3. Hemorrhage is also a problem with minimally invasive surgery (laparoscopic surgery and the like), and switching to incisive surgery may be necessary when hemorrhage cannot be sufficiently prevented.

The following methods exist for hemostasis.

1. Methods of directly compressing the blood vessels at the site of hemorrhage (astriction). The drawback to this method is that time and effort are required to maintain pressure, while the patient is also at risk of hematoma.

2. Other methods of arresting hemorrhage by physical means, such as methods of clamping or clipping near the site of hemorrhage, or methods of placing a plug or sponge on the site of hemorrhage. The drawback to these hemorrhage arresting methods is difficulty of management when the hemorrhaging is from numerous microvessels.

3. Methods of clotting the blood by heat and cauterizing the hemorrhaging blood vessel (electrocautery). The drawback of such methods is that the surrounding tissue is subjected to thermal injury and the patient undergoes increased invasion, while the medical instruments used require expert skill (the method cannot be used outside of a medical institution).

The following agents exist for hemostasis.

1. Alginic acid
2. Gelatin sponges
3. Collagen fibers
4. Fibrin paste

Collagen fibers and fibrin paste are often clinically used as effective hemorrhage arresting materials, but their drawbacks include the fact that (1) gelatin and collagen fibers are animal collagen and fibrin paste is an animal-derived product obtained using a blood preparation and bovine thrombin, and therefore the risk of infection exists, and (2) they are non-transparent and therefore interfere at the site of surgery.

Heparinemia may sometimes be induced, wherein the blood clotting function of the patient is artificially reduced during surgery. Heparin is used to suppress blood clotting during surgery when using an artificial heart-lung machine. An artificial heart-lung machine is foreign to the body, and when blood is circulated through the artificial heart-lung machine the blood immediately coagulates and clogs the circuit, so that administration of heparin into the blood is essential before extracorporeal circulation.

Collagen fibers and fibrin paste utilize the blood clotting system of the body for hemostasis, and therefore have a lower hemostatic effect for heparinemia. A lower hemostatic effect tends to lead to greater hemorrhage and thus increased need for blood transfusion, while a longer time is also required for complete hemostasis when extracorporeal circulation is terminated. Thus, a hemorrhage arresting material has been desired that does not have lower performance with heparinemia and that does not utilize blood clotting.

Blood vessel suture is necessary not only for cardiac and vascular surgery, but also for general intraperitoneal surgery. Since a small amount of blood leakage occurs from blood vessel sutures following operation, a hemorrhage arresting material with a persistent suppressing effect is desired.

Biliary or pancreatic fistula is a symptom wherein leakage of bile or pancreatic fluid due to biliary system surgery or pancreatitis or pancreatic surgery adversely affects other organs. Currently, no substance is known that effectively inhibits leakage of bile or pancreatic fluid and is clinically applicable, and therefore a method for safely and effectively preventing biliary and pancreatic fistula is desired.

Also, leakage of air in the lungs is known as a symptom of spontaneous pneumothorax involving rupture of the alveolar cyst, or traumatic pneumothorax occurring with rib fracture or catheter paracentesis. Depending on the symptoms it may be necessary to wait for natural healing, and a method of simply providing an upper layer on the affected area and adhering it to the lung tissue to occlude the cyst hole is considered a simple and highly safe method for treatment of pneumothorax.

Techniques for endoscopic excision of lesions continue to be developed with advances in endoscope technology. In particular, surgical methods are being established for endoscopic excision of lesions of polyps or early-stage cancer in the gastrointestinal tract, including the esophagus, stomach and intestines (superficial cancer believed to be without lymph node metastasis). In endoscopic demucosation, hypertonic saline or the like is usually injected into the submucous layer including the lesion site to swell the lesion site, and the excision site is held while excising the tissue containing the lesion site by electrocautery, for example.

In this technique, a solution such as hypertonic saline is injected into the submucous layer to separate the lesion site from the proper muscle layer, but low-viscosity solutions such as saline cannot maintain lesion site swelling during surgery, and therefore an infusion solution that allows swelling of affected areas to be maintained during the course of surgery is desired.

Methods of suppressing hemorrhage from lesion excision sites by injection of a vasoconstrictor such as thrombin through a catheter are also employed, but no effective measures for complete hemostasis have been established, and therefore a method for rapidly stopping post-excision hemorrhage is also desired.

Advances in catheter treatments have led to establishment of surgical methods for killing tumors or myomas by occlusion of the arteries flowing into lesion sites, that control the blood flow to the tumors and myomas. Specifically, these include hepatic artery occlusion, uterine artery occlusion and cerebral artery occlusion.

In such techniques, collagen extracted from a heterogeneous animal, or a liquid such as ethylene-vinyl alcohol, is infused for occlusion of the artery, but this raises concerns regarding risk of infection and toxicity. The development of an infusion solution with no risk of infection and low toxicity is therefore desired.

An infusion solution that may contain an added anticancer agent or contrast agent is also desired.

Self-assembling peptides have a property whereby the peptide molecules form regularly arranged self-assemblies according to their amino acid sequence. In recent years, these have attracted much attention as novel materials because of their physical, chemical and biological properties.

Self-assembling peptides have an alternating structure of electrically charged hydrophilic amino acids and electrically neutral hydrophobic amino acids, and alternating distribution of positive charge and negative charge, whereby they adopt a β-structure at physiological pH and salt concentration.

Hydrophilic amino acids that can be used include acidic amino acids such as aspartic acid and glutamic acid, and basic amino acids such as arginine, lysine, histidine and ornithine. As hydrophobic amino acids there may be used alanine, valine, leucine, isoleucine, methionine, phenylalanine, tyrosine, tryptophan, serine, threonine or glycine.

The self-assembly of such peptides occurs under the following conditions.

(1) The peptide molecules adopt a β-structure in aqueous solution, wherein the charged hydrophilic amino acids and electrically neutral hydrophobic amino acids are maldistributed on the two sides of the peptide molecules.

(2) The β-structure results in a complementary electrical distribution between adjacent molecules.

(3) The β-structure leads to sufficient hydrophobic bonding between adjacent molecules.

(4) The electrical charge of the amino acid side chains is screened by monovalent inorganic salts.

(5) The molecules are electrostatically neutral near the isoelectric point of the peptide.

It is believed that self-assembly occurs by the following mechanism when these conditions are all satisfied.

(1) The alternating distribution of positive charge and negative charge in the peptide molecules causes attraction between the molecules.

(2) Hydrophobic bonds are formed between the neutral amino acid side chains of adjacent molecules.

(3) The positive/negative electrical distribution results in complementary alignment between adjacent molecules, and associative force between the molecules is strengthened.

(4) The molecular aggregates gradually extend, forming nanofibers.

The nanofibers are superfine fibers with thicknesses of about 10 nm-20 nm, and it has been reported that they aggregate to form meshwork and exhibit a macroscopically gel-like form.

The gel network structure strongly resembles a natural extracellular matrix (ECM) in terms of its fiber size and pore size, and its use as a scaffold for cell culture is being studied.

Since the peptide hydrogel is biodegradable and its decomposition product does not adversely affect tissue, while it is also highly bioabsorbable, it is suitable for cellular engraftment and growth.

Because self-assembling peptides are chemical synthetic products obtained by solid phase synthesis and do not carry the risk of animal-derived infectious disease, they are even more promising as substitutes for collagen and the like, given concerns in recent years regarding animal viruses and other unknown infectious agents, such as mad cow disease.

The application of self-assembling peptides for hemostasis is indicated in Patent document 1, but the video showing hemostasis at a hepatic incision site, provided in an article cited in the examples thereof, shows persistent blood leakage from the end of the incision site, and the reported complete hemostasis was not achieved. It is conjectured that the reason for incomplete hemostasis was insufficient adhesion between the self-assembling peptide gel and the tissue. Thus, further improvement is necessary to take advantage of the hemostatic effect of self-assembling peptides to a level allowing their clinical application.

[Patent document 1] International Patent Publication No. WO2006-116524

DISCLOSURE OF THE INVENTION

Problems to be Solved by the Invention

The objective of the present invention is to provide a self-assembling peptide tissue occluding agent that can effectively occlude sites of tissue damage in large mammals including humans and that does not carry the risk of infection by viruses and the like, as well as a method for use of the same.

Means for Solving the Problems

The present inventors have completed this invention upon finding that a tissue occluding effect equivalent to or greater than that of existing tissue occluding agents is exhibited when a self-assembling peptide hydrogel utilized as a scaffold for cell culture is applied for tissue occlusion. It has been a noted issue that simply applying aqueous peptide solutions to body fluid leakage sites does not provide a sufficient tissue occluding effect. As a result of diligent research, however, it was found that a sufficient tissue occluding effect and biological safety can be achieved by removing excess body fluid from body fluid leakage sites.

Specifically, the invention relates to a tissue occluding agent containing a peptide, wherein the peptide is an amphiphilic peptide having 8-200 amino acid residues with the hydrophilic amino acids and hydrophobic amino acids alternately bonded, and is a self-assembling peptide exhibiting a β-structure in aqueous solution in the presence of physiological pH and/or a cation.

In this tissue occluding agent, the peptide is preferably a self-assembling peptide having a repeating sequence which is a sequence comprising arginine, alanine, aspartic acid and alanine, a sequence comprising isoleucine, glutamic acid, isoleucine and lysine, or a sequence comprising lysine, leucine, aspartic acid and leucine, and more preferably it is a self-assembling peptide comprising the amino acid sequence listed as SEQ ID NO: 1, SEQ ID NO: 2 or SEQ ID NO: 3.

The tissue occluding agent also preferably comprises small molecular drugs to prevent hemolysis, inflammation and infection.

The small molecular drugs are preferably selected from the group consisting of glucose, saccharose, purified saccharose, lactose, maltose, trehalose, dextran, iodine, lysozyme chloride, dimethylisopropylazulene, tretinoin tocoferil, povidone iodine, alprostadil alfadex, anise alcohol, isoamyl salicylate, α,α-dimethylphenylethyl alcohol, bacdanol, helional, sulfazin silver, bucladesine sodium, alprostadil alfadex, gentamycin sulfate, tetracycline hydrochloride, sodium fusidate, mupirocin calcium hydrate and isoamyl benzoate.

The invention also relates to agents comprising the aforementioned tissue occluding agent, which are hemostatic agents for hemorrhage of blood that have reduced coagulating power due to addition of anticoagulants, hemostatic agents for hemorrhage wound surfaces on parenchymal organs, hemostatic agents for arterial hemorrhage and phleborrhagia, inhibitors of bile leakage from the gall bladder or bile duct, inhibitors of hemorrhage or air leakage from the lungs, hemostatic agents or transcatheter application during endoscopic demucosation, infusions for mucosal tissue for swelling of excision sites, inhibitors of hemorrhage and body fluid leakage from excision sites in methods of excising mucosal tissue resections that have been swelled by infusion of liquids into the mucosal tissue, or arteriovenous occluding agents in arteriovenous occlusion or varix sclerotherapy agents used in varix sclerotherapy. Anticancer agents and/or contrast agents may also be added to the arteriovenous occluding agent or varix sclerotherapy agent.

EFFECT OF THE INVENTION

The self-assembling peptide as the major component in the tissue occluding agent of the invention can also serve as a scaffold for migrating cells in addition to its role as a occluding agent, thus allowing it to have a higher curative effect after surgery instead of simple occlusion. In addition, the tissue occluding agent of the invention has improved adhesion to tissue when excess body fluid has been removed from a body fluid leakage site (for example, when it has been applied to a hemorrhage arrest site where hemorrhage has been stopped), and thus exhibits an adequate tissue occluding effect with biological safety.

The self-assembling peptide as the major component of the tissue occluding agent of the invention can be produced by synthesis, and therefore does not carry the risk of viral or other infection compared to conventional tissue-derived biomaterials, and is itself bio absorbable, eliminating concerns of inflammation.

coating 2% aqueous peptide solution (arrow tip), (c) no hemorrhage from incision site after rinsing with physiological saline (arrow tip).

Figure 10:
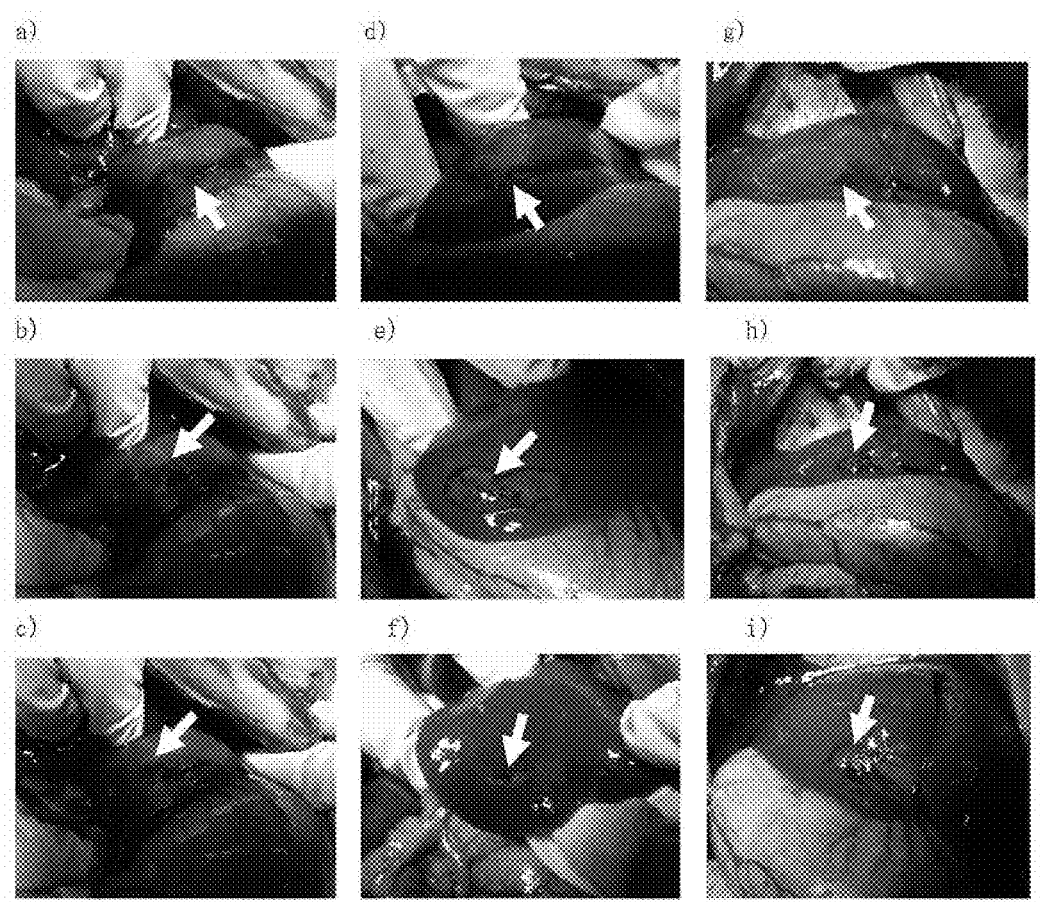

FIG. 10 shows the hemostatic effect of a 1% aqueous peptide solution in a hepatic transection model. (a) Hemorrhage confirmed after hepatic incision (arrow tip), (b) coating 1% IEIK9 (SEQ ID NO:4; SEQ ID NO: 9) aqueous peptide solution (arrow tip), (c) hemorrhage observed from incision site after rinsing with physiological saline (arrow tip), (d) hemorrhage confirmed after hepatic incision (arrow tip), (e) coating 1% IEIK13 (SEQ ID NO:2; SEQ ID NO:8) aqueous peptide solution (arrow tip), (f) no hemorrhage observed from incision site after rinsing with physiological saline (arrow tip), (g) hemorrhage confirmed after hepatic incision (arrow tip), (h) coating 1% KLD (SEQ ID NO:3; SEQ ID NO:11) aqueous peptide solution (arrow tip), (i) no hemorrhage observed from incision site after rinsing with physiological saline (arrow tip).

Figure 11:
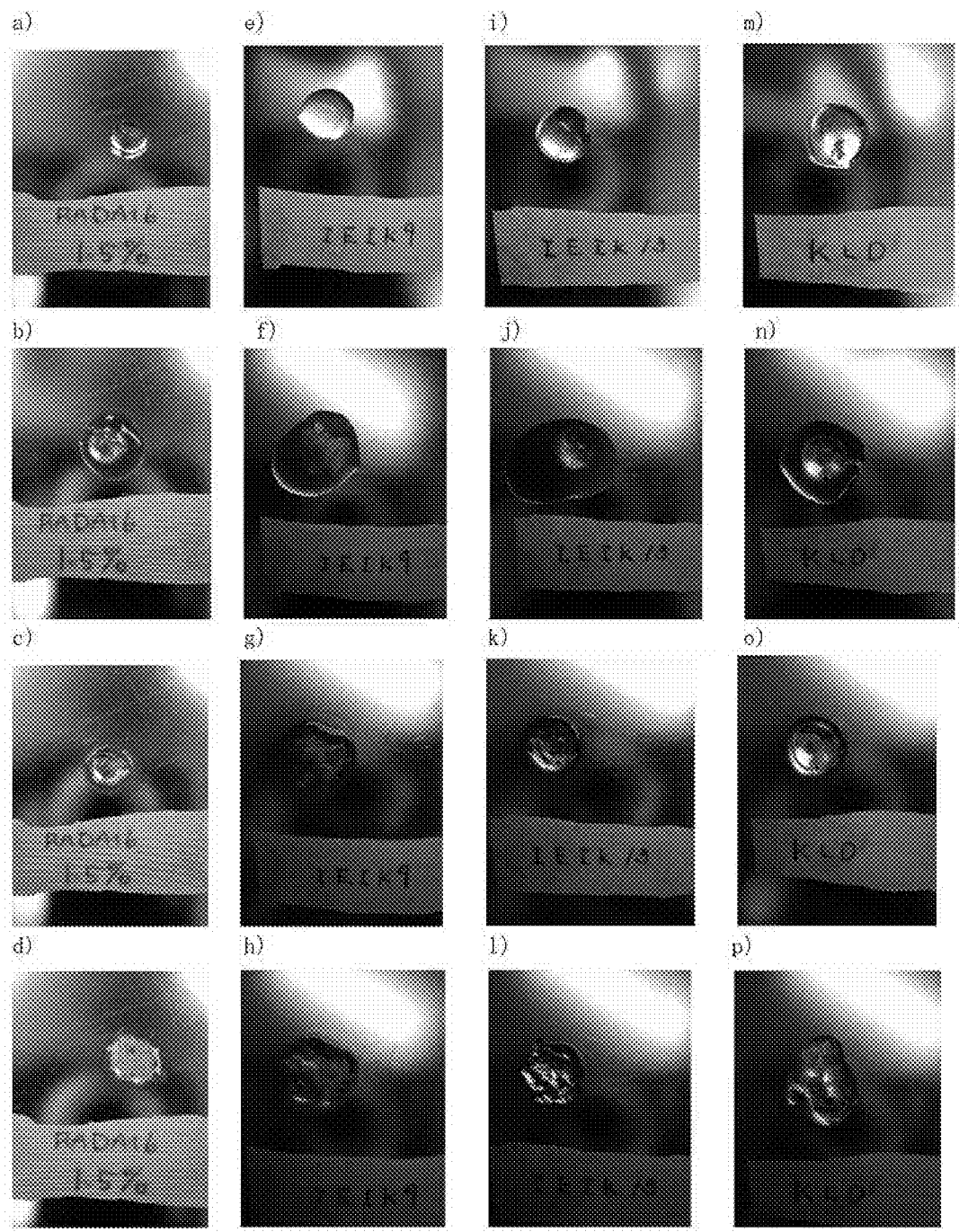

FIG. 11 shows self-assembling of a 1.5% aqueous peptide solution by bile. (a) 1.5% PuraMatrix aqueous peptide solution before self-assembling, (b) 1.5% PuraMatrix aqueous peptide solution after coating bile, (c) bile removed, self-assembly confirmed, (d) physical impact applied to disrupt self-assembled gel, (e) 1% IEIK9 (SEQ ID NO: 4; SEQ ID NO:9) aqueous peptide solution before self-assembly, (f) 1% IEIK9 (SEQ ID NO: 4; SEQ ID NO:9) aqueous peptide solution after coating bile, (g) virtually no self-assembly seen after removal of bile, (h) physical impact applied to disrupt self-assembled gel, (i) 1% IEIK13 (SEQ ID NO: 2; SEQ ID NO:8) aqueous peptide solution before self-assembly, (j) 1% IEIK13 (SEQ ID NO: 2; SEQ ID NO:8) aqueous peptide solution after coating bile, (k) bile removed, self-assembly confirmed, (l) physical impact applied to disrupt self-assembled gel, (m) 1% KLD (SEQ ID NO:3; SEQ ID NO:11) aqueous peptide solution before self-assembly, (n) 1% KLD (SEQ ID NO:3; SEQ ID NO:11) aqueous peptide solution after coating bile, (o) bile removed, self-assembly confirmed, (p) physical impact applied to disrupt self-assembled gel.

Figure 12:
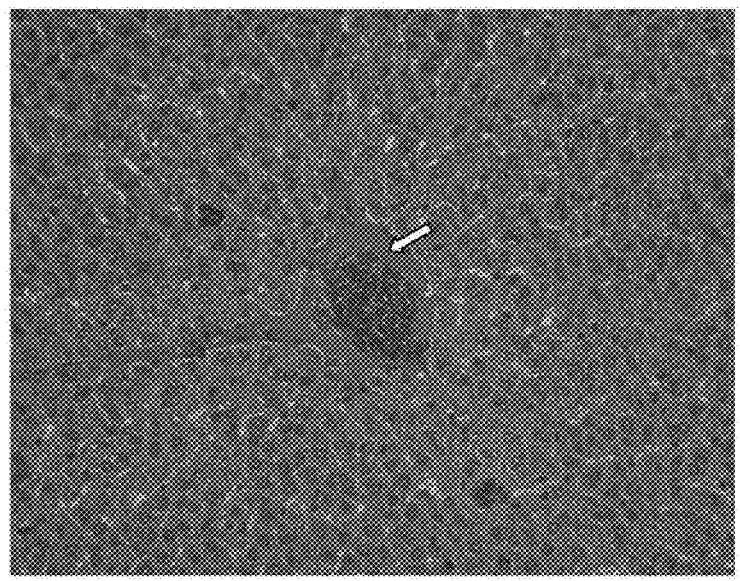
Figure 12:
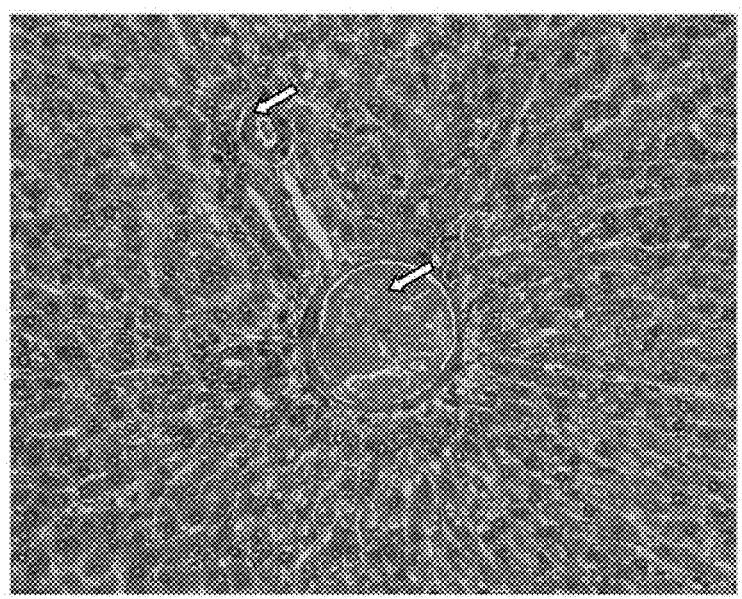

FIG. 12 shows the portal vein embolization effect with a 3% aqueous peptide solution. (a), (b) Embolization of portal vein confirmed (arrow tip).

Figure 13:
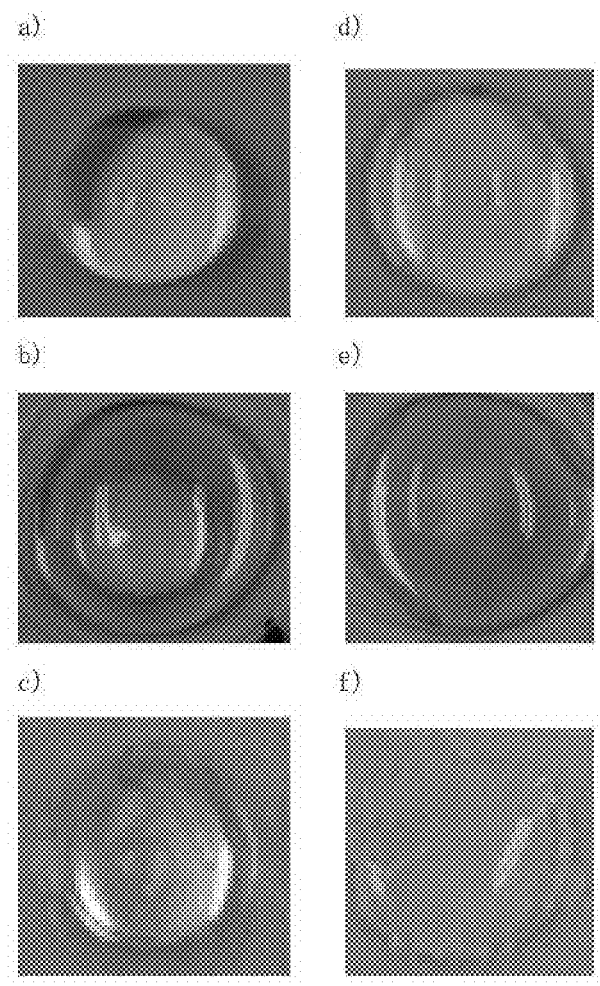

FIG. 13 shows self-assembly of an iopamidol-containing aqueous peptide solution.
(a) Iopamidol-containing 3% aqueous peptide solution before self-assembly, (b) iopamidol-containing 3% aqueous peptide solution after coating cell culturing medium, (c) cell culturing medium removed, self-assembly confirmed, (d) iopamidol-containing 0.0468% aqueous peptide solution before self-assembly, (e) iopamidol-containing 0.0468% aqueous peptide solution after coating cell culturing medium, (f) cell culturing medium removed, self-assembly confirmed.

Figure 14:
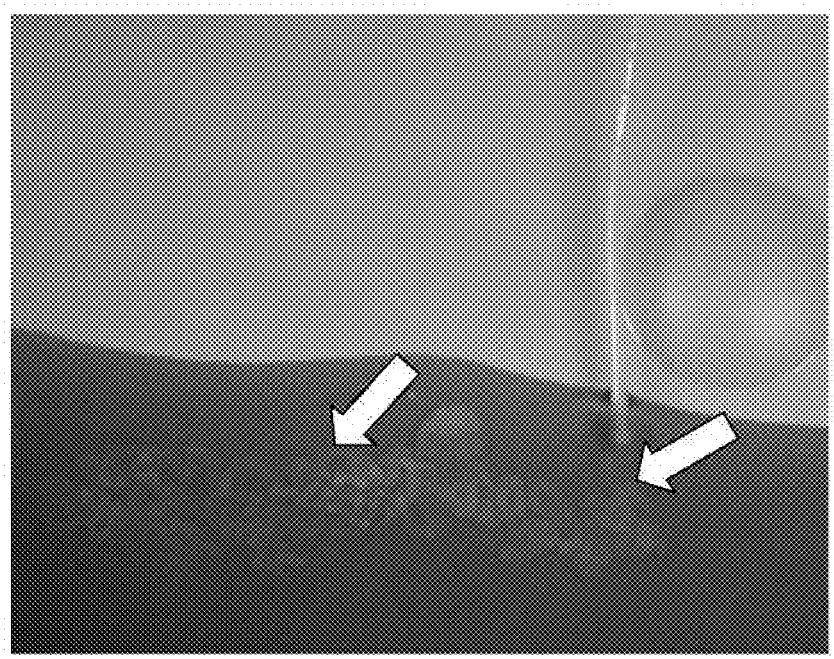

FIG. 14 shows self-assembly of an iopamidol-containing 3% aqueous peptide solution after catheter passage (arrow tip).

BEST MODE FOR CARRYING OUT THE INVENTION

The tissue occluding agent of the invention will now be explained in detail.

The main component of the tissue occluding agent of the invention is a self-assembling peptide which is an amphiphilic peptide having 8-200 amino acid residues with the hydrophilic amino acids and hydrophobic amino acids alternately bonded, and it exhibits a β-structure in aqueous solution in the presence of physiological pH and/or a cation.

According to the invention, physiological pH is pH 6-8, preferably pH 6.5-7.5 and more preferably pH 7.3-7.5. A "cation" according to the invention is, for example, 5 mM-5 M sodium ion or potassium ion.

Self-assembling peptides used for the invention can be represented by the following 4 general formulas, for example.

$$((XY)_l\text{—}(ZY)_m)_n \quad (I)$$

$$((YX)_l\text{—}(YZ)_m)_n \quad (II)$$

$$((ZY)_l\text{—}(XY)_m)_n \quad (III)$$

$$((YZ)_l\text{—}(YX)_m)_n \quad (IV)$$

(In formulas (I)-(IV), X represents an acidic amino acid, Y represents a hydrophobic amino acid and Z represents a basic amino acid, and l, m and n are all integers (n×(l+m)<200)).

The N-terminals may be acetylated, and the C-terminals may be amidated.

Hydrophilic amino acids that can be used include acidic amino acids such as aspartic acid and glutamic acid, and basic amino acids such as arginine, lysine, histidine and ornithine. As hydrophobic amino acids there may be used alanine, valine, leucine, isoleucine, methionine, phenylalanine, tyrosine, tryptophan, serine, threonine or glycine.

Preferred among these self-assembling peptides are self-assembling peptides having the repeating sequence of arginine, alanine, aspartic acid and alanine (RADA, SEQ ID NO:5), and such peptide sequences are represented by Ac-(RADA)$_p$-CONH$_2$ (p=2-50). There are also preferred self-assembling peptides having the repeating sequence of isoleucine, glutamic acid, isoleucine and lysine (IEIK, SEQ ID NO:7), and such peptide sequences are represented by Ac-(IEIK)$_p$I—CONH$_2$ (p=2-50). There are additionally preferred self-assembling peptides having the repeating sequence of lysine, leucine, aspartic acid and leucine (KLDL, SEQ ID NO:10), and such peptide sequences are represented by Ac-(KLDL)$_p$-CONH$_2$ (p=2-50). These self-assembling peptides may be composed of 8-200 amino acid residues, with 8-32 residue self-assembling peptides being preferred and self-assembling peptides having 12-16 residues being more preferred.

As specific examples of self-assembling peptides according to the invention there may be mentioned peptide RAD16-I having the sequence (Ac-(RADA)$_4$-CONH$_2$) (SEQ ID NO:1), peptide IEIK13 having the sequence (Ac-(IEIK)$_3$I—CONH$_2$) (SEQ ID NO:2) and peptide KLD having the sequence (Ac-(KLDL)$_3$-CONH$_2$) (SEQ ID NO:3), and a 1% aqueous solution of RAD16-I is available as the product PuraMatrix™ by 3D-Matrix Co., Ltd. PuraMatrix™ contains 1% peptide having the sequence (Ac-(RADA)$_4$-CONH$_2$) (SEQ ID NO:1), with hydrogen ion and chloride ion.

PuraMatrix™, IEIK13 (SEQ ID NO:2; SEQ ID NO:8) and KLD (SEQ ID NO:3; SEQ ID NO:11) are oligopeptides of 12-16 amino acid residues and having a length of about 5 nm, and although their solutions are liquid at acidic pH, the peptides undergo self-organization upon change to neutral pH, forming nanofibers with diameters of about 10 nm, causing gelling of the peptide solutions.

PuraMatrix™ is an amphiphilic peptide having an amino acid sequence with alternate repeats of positively charged arginine and negatively charged aspartic acid as hydrophilic amino acids, and alanine as a hydrophobic amino acid, IEIK13 (SEQ ID NO:8) is an amphiphilic peptide having an amino acid sequence with alternate repeats of positively charged lysine and negatively charged glutamic acid as hydrophilic amino acids and isoleucine as a hydrophobic amino acid, and KLD (SEQ ID NO:11) is an amphiphilic peptide having an amino acid sequence with alternate repeats of positively charged lysine and negatively charged aspartic acid as hydrophilic amino acids and leucine as a hydrophobic amino acid; the self-assembly of the peptides is due to hydrogen bonding and hydrophobic bonding between the peptide molecules by the amino acids composing the peptides.

In the self-assembling peptides used for the invention, the nanofiber diameter is 10-20 nm and the pore size is 5-200 nm, as averages. These numerical value ranges are approximately the same as collagen, which is a natural extracellular matrix.

Physiological pH and salt concentration are conditions for self-assembly of the self-assembling peptides of the invention. The presence of a monovalent alkali metal ion is especially important. That is, sodium ion and potassium ion present in the body in large amounts in the body help promote gelling. Once gelling has occurred, the gel does not decompose even under common protein denaturing conditions such as high temperature or with denaturing agents such as acids, alkalis, proteases, urea, guanidine hydrochloride or the like.

These self-assembling peptides, such as PuraMatrix™, are peptide sequences lacking a distinct physiologically active motif, and therefore intrinsic cell function is not impaired. Physiologically active motifs control numerous intracellular phenomena such as transcription, and the presence of physiologically active motifs can lead to phosphorylation of intracytoplasmic or cell surface proteins by enzymes that recognize the motifs. When a physiologically active motif is present in a peptide tissue occluding agent, transcription of proteins with various functions can be activated or suppressed. The self-assembling peptides, such as PuraMatrix™, lack such physiologically active motifs and therefore do not carry this risk.

Since the self-assembling peptide used for the invention is produced by chemical synthesis, it does not contain unidentified components derived from the extracellular matrix of another animal. This property therefore eliminates concerns of infection, including BSE, making the peptide highly safe even for medical use.

Furthermore, a self-assembling peptide composed of natural amino acids also has satisfactory biocompatibility and biodegradability, and it has been reported that infusion of PuraMatrix™ into murine cardiac muscle, for example, results in infiltration of cells into the PuraMatrix™ and formation of normal tissue. The decomposition time differs depending on the conditions such as the location of infusion, but the fibers decompose and are excreted by about 2 to 8 weeks after infusion.

The tissue occluding agent of the invention may further contain added small molecular drugs. There are no particular restrictions on such small molecular drugs, and there may be mentioned glucose, saccharose, purified saccharose, lactose, maltose, trehalose, dextran, iodine, lysozyme chloride, dimethylisopropylazulene, tretinoin tocoferil, povidone iodine, alprostadil alfadex, anise alcohol, isoamyl salicylate, α,α-dimethylphenylethyl alcohol, bacdanol, helional, sulfazin silver, bucladesine sodium, alprostadil alfadex, gentamycin sulfate, tetracycline hydrochloride, sodium fusidate, mupirocin calcium hydrate and isoamyl benzoate.

A sugar may be added to the tissue occluding agent of the invention to improve the osmotic pressure of the solution from hypotonicity to isotonicity without reducing the tissue occluding effect, thereby allowing the biological safety to be increased.

The tissue occluding agent of the invention may be in the form of a powder, a solution, a gel, or the like. Since the self-assembling peptide gelates in response to changes in solution pH and salt concentration, it can be distributed as a liquid drug that gelates upon contact with the body during application.

Modes of clinical use include cylinder-equipped syringes or pipettes that are prefilled with chemical solution containing components such as self-assembling peptides (prefilled syringes), or methods of supplying a chemical solution to a syringe or pipette chip by means that supplies the components through the opening of the syringe or pipette chip (an aspirator or valve), and applying it to the affected area through the discharge section. A construction with two or more syringes or pipettes is sometimes used.

The components may be used as a coating on an instrument such as a stent or catheter, to suppress body fluid leakage.

Also, the components may be anchored on a support such as gauze or a bandage, or a lining, that is commonly used in the field. The components may also be soaked into a sponge for use.

In addition, an atomizing sprayer filled with a powder or solution of the components may be prepared. When such a spray is used for spraying onto an affected area, the pH and salt concentration increase upon contact with the body causing gelling, and therefore this form can be applied for a greater variety of sites and conditions than a gel form.

The tissue occluding agent of the invention will now be explained in greater detail through the following examples, but the invention is not limited thereto so long as its gist and range of application is maintained.

EXAMPLE 1

Hemostatic Effects of 1% Aqueous Peptide Solution and 3% Aqueous Peptide Solution in Rabbit Abdominal Aorta/Portal Vein Stem Injection Needle Perforation Model A rabbit abdominal aorta and portal vein stem injection needle perforation model was prepared under vascular clamp, and the hemostatic effects of 1% aqueous peptide solution and 3% aqueous peptide solution were evaluated.
<Materials>
Aqueous Peptide Solutions
1. 1% Aqueous peptide solution (peptide sequence: Ac-(RADA)$_4$-NH$_2$ (SEQ ID NO:1), CPC Scientific, Inc; concentration: wt/vol)
2. 3% Aqueous peptide solution (peptide sequence: Ac-(RADA)$_4$-NH$_2$ (SEQ ID NO:1), CPC Scientific, Inc; concentration: wt/vol)
Animals
Japanese white rabbits (3.0-4.0 kg, Japan White, conventional, purchased from Funabashi Farm Co., Ltd.). The animals were bred with breeding pellets (JA Higashinihon Kumiai Shiryou) supplied in a breeding room controlled at a room temperature of 25° C., a humidity of 65% and an illumination time of 12 hours (7:00-19:00), and water freely supplied with a water bottle. Fasting was from the morning of the test day, with water freely supplied.
<Method>
The rabbits were subcutaneously administered (3 mg/kg) Celactar 2% injection (2.0 g content as xylazine in 100 mL, product of Bayer Ltd.), and then ketamine (50 mg content as ketamine in 1 mL, product of Fuji Chemical Industries, Ltd.) was intravenously administered (10 mg/kg) for anesthesia.

The rabbits were laparotomized by median section. Approximately 10 cm of the abdominal aorta and portal vein stem was exposed, each blood vessel was ablated from the surrounding tissue, and the abdominal aorta was punctured with a 23G injection needle (Terumo Corp.) while the portal vein stem was punctured with a 26G injection needle (Terumo Corp.).

Upon confirming hemorrhage, blood flow at the peripheral end and central end was clamped with a hemostatic clamp, and after removing the hemorrhaged blood with physiological saline and gauze, it was immediately treated with the aqueous peptide solution.

After 1-2 minutes of treatment, blood flow was released and the presence of hemorrhage from the puncture site was visually examined.

<Results>

Figure 1:
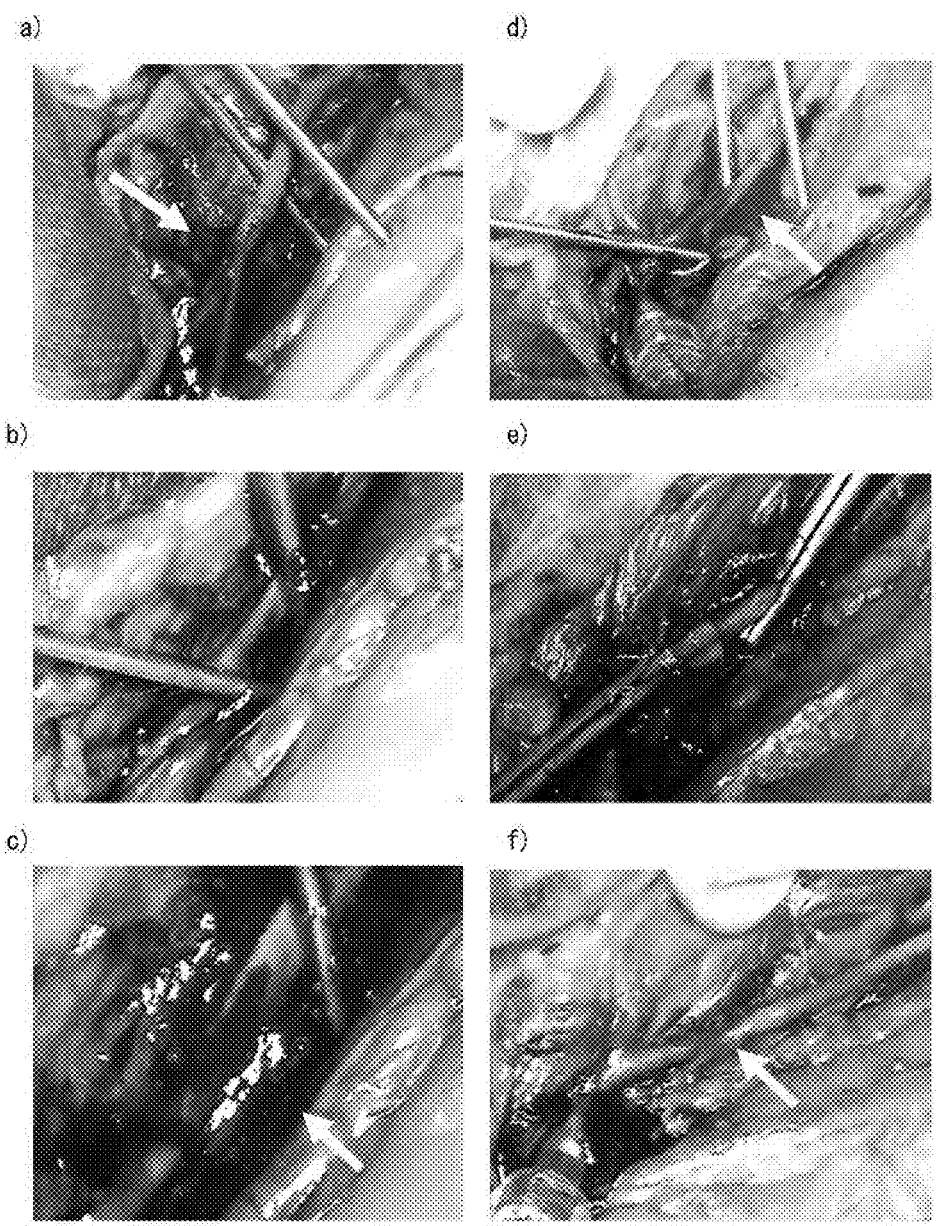
FIG. 1 shows a comparison between the hemostatic effects of a 1% aqueous peptide solution and 3% aqueous peptide solution in a abdominal aorta injection needle perforation model. (a) Hemorrhage confirmed following aortal puncture, perivascular hemorrhage (arrow tip; 1% aqueous peptide solution-treated group), (b) coating aqueous peptide solution (1% aqueous peptide solution-treated group), (c) blood vessel indiscernible due to blood of resumed hemorrhage following declamp (arrow tip; 1% aqueous peptide solution-treated group), (d) hemorrhage confirmed following aortal puncture, perivascular hemorrhage (arrow tip; 3% aqueous peptide solution-treated group), (e) coating aqueous peptide solution (3% aqueous peptide solution-treated group), (f) after rinsing with physiological saline, completely hemorrhage-arrested blood vessel can be seen at center of photograph (arrow tip; 3% aqueous peptide solution-treated group).

FIG. 1 shows the hemostatic effect of the aqueous peptide solution on hemorrhage from the blood vessel in this example. As seen in Table 1, two of two rabbits of the abdominal aorta perforation model demonstrated complete hemostasishemostasis with 3% aqueous peptide solution. With 1% aqueous peptide solution, however, both rabbits had projectile hemorrhage following release of the clamp, and therefore hemostasis was not complete. hemostasis In the portal vein stem perforation model, two of two cases also demonstrated complete hemostasis with 3% aqueous peptide solution, but had persistent phleborrhagia with 1% aqueous peptide solution.

TABLE 1

| No. | Aqueous peptide solution | Puncture site | Procedure time | Result | Observations |
|---|---|---|---|---|---|
| 1 | 3% | Abdominal aorta | 1:00 | G | Complete hemostasis |
| 2 | 3% | Abdominal aorta | 1:00 | G | Complete hemostasis |
| 3 | 1% | Abdominal aorta | 2:00 | P | Projectile hemorrhage following release of blockage |
| 4 | 1% | Abdominal aorta | 2:00 | P | Projectile hemorrhage following release of blockage |
| 5 | 3% | Portal vein stem | 2:00 | G | Complete hemostasis |
| 6 | 3% | Portal vein stem | 1:00 | G | Complete hemostasis |
| 7 | 1% | Portal vein stem | 2:00 | P | Continuous hemorrhage following release of blockage |

EXAMPLE 2

Hemostatic Effects of 1% Aqueous Peptide Solution and 3% Aqueous Peptide Solution in Rabbit Partial Liver Resection Model A rabbit partial liver resection model was prepared and the hemostatic effects of 1% aqueous peptide solution and 3% aqueous peptide solution were evaluated.

<Materials>

Aqueous Peptide Solutions 1. 1% Aqueous peptide solution (peptide sequence: Ac-(RADA)$_4$-NH$_2$ (SEQ ID NO:1), CPC Scientific, Inc.)

2. 3% Aqueous peptide solution (peptide sequence: Ac-(RADA)$_4$-NH$_2$ (SEQ ID NO:1), CPC Scientific, Inc.)

Animals

Japanese white rabbits (3.0-4.0 kg, Japan White, conventional, purchased from Funabashi Farm Co., Ltd.). The animals were bred with breeding pellets (JA Higashinihon Kumiai Shiryou) supplied in a breeding room controlled to a room temperature of 25° C., a humidity of 65% and an illumination time of 12 hours (7:00-19:00), and water freely supplied with a water bottle. Fasting was from the morning of the test day, with water freely supplied.

<Method>

The rabbits were subcutaneously administered (3 mg/kg) Celactar 2% injection (2.0 g content as xylazine in 100 mL, product of Bayer Ltd.), and then ketamine (50 mg content as ketamine in 1 mL, product of Fuji Chemical Industries, Ltd.) was intravenously administered (10 mg/kg) for anesthesia.

The rabbits were laparotomized by median section, and the hepatic left or right lobe was sharply excised to a size of approximately 5 cm width×3 cm length from the edge using a scalpel, to prepare a liver section.

After confirming projectile hemorrhage from the resected surface, the liver parenchyma including the arteries, portal vein and veins was manually astricted to immediately block blood flow, and the hemorrhaged blood was removed with physiological saline and gauze, after which the prepared resected liver surface was treated with aqueous peptide solution.

Blood flow was released 1-2 minutes after treatment, the aqueous peptide solution that was gelled was removed by physiological saline, and the presence of any hemorrhage from the resected liver surface s was visually confirmed.

The resected liver surface in which a hemostatic effect was seen were fixed with 20% formalin and histopathologically evaluated by HEstaining.

<Results>

Figure 2:
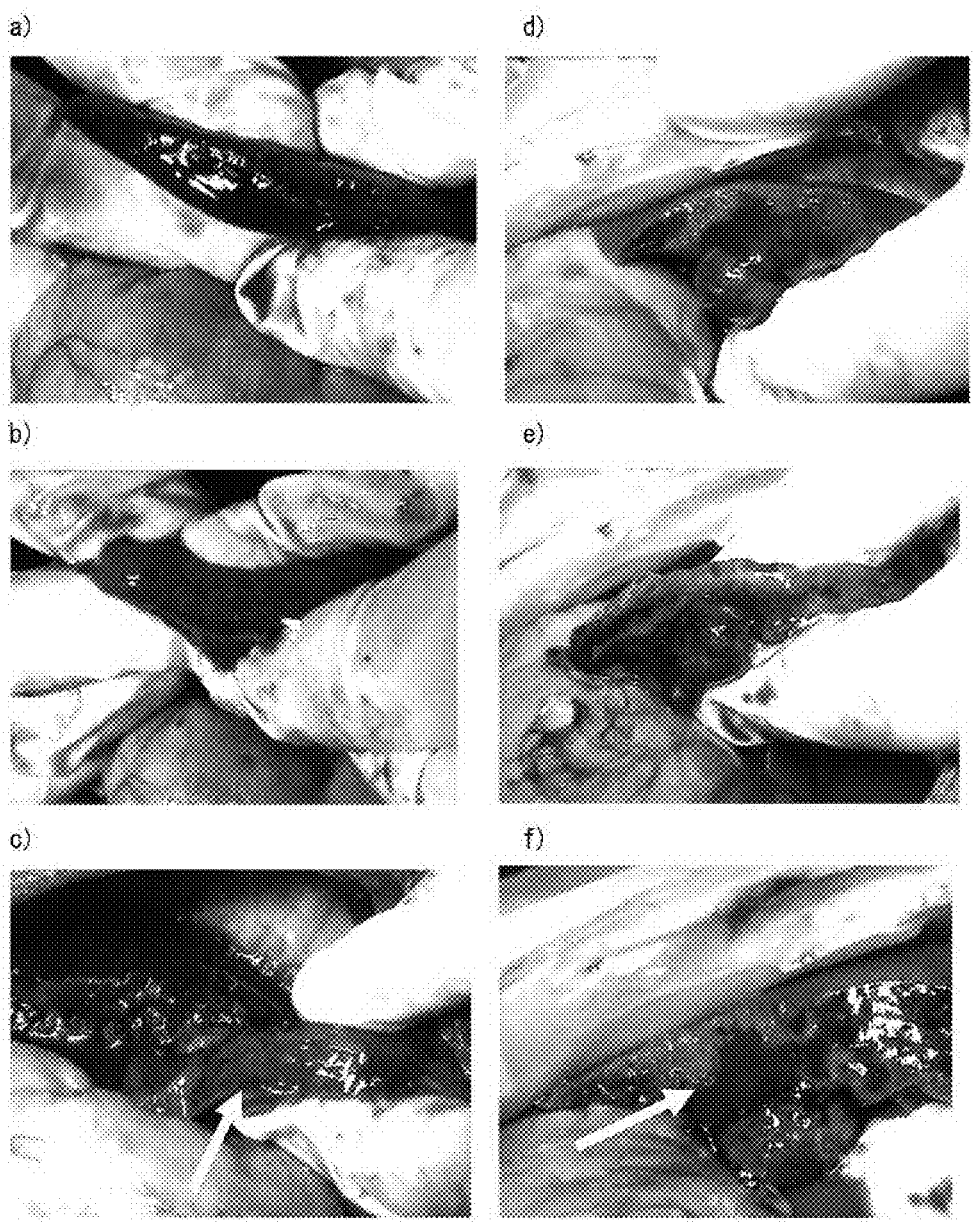
FIG. 2 shows a comparison between the hemostatic effects of a 1% aqueous peptide solution and 3% aqueous peptide solution in a hepatic partial excision model. (a) Hemorrhage confirmed following hepatic excision (1% aqueous peptide solution-treated group), (b) coating aqueous peptide solution (1% aqueous peptide solution-treated group), (c) no hemorrhage observed from cut surface after rinsing with physiological saline (arrow tip; 1% aqueous peptide solution-treated group), (d) hemorrhage confirmed following hepatic excision, (3% aqueous peptide solution-treated group), (e) coating aqueous peptide solution (3% aqueous peptide solution-treated group), (f) hemorrhage observed from cut surface after rinsing with physiological saline (arrow tip; 3% aqueous peptide solution-treated group).
Figure 3:
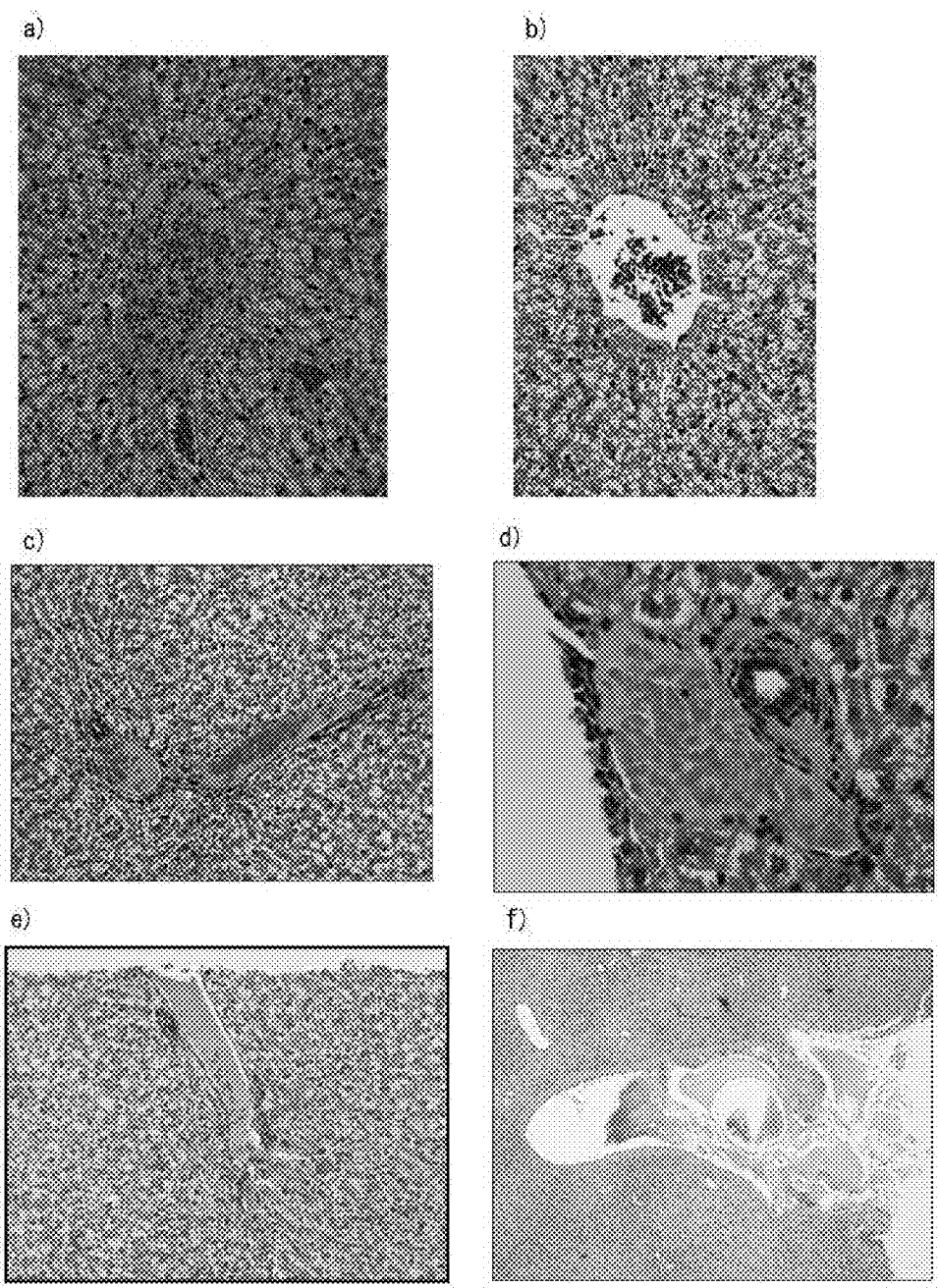
FIG. 3 shows a histopathological comparison of the cut surfaces of a liver with arrested hemorrhage using an aqueous peptide solution and liver from a control group (physiological saline). (a) Intravascular histology (aqueous peptide solution-treated group), (b) intravascular histology (physiological saline-treated group), (c) intravascular histology (aqueous peptide solution-treated group), (d) intravascular histology (aqueous peptide solution-treated group), (e) intravascular histology (aqueous peptide solution-treated group), (f) intravascular histology (aqueous peptide solution-treated group).

FIG. 2 shows the hemostatic effect of the aqueous peptide solutions on hemorrhage from the resected liver surface in this example. As seen in Table 2, two of two rabbits showed a complete hemostasis with 1% aqueous peptide solution, but a complete hemostasis was observed in only 1 of 4 rabbits with 3% aqueous peptide solution. In histological observation, blood vessel occlusion was confirmed in the vascular surface due to tight contact of the gelled aqueous peptide solution to the resected liver surface (FIG. 3).

TABLE 2

| No. | Concentration | Procedure time | Result | Observations |
|---|---|---|---|---|
| 1 | 3% | 2:00 | P | Continuous hemorrhage from aorta |
| 2 | 3% | 2:00 | G | Complete hemostasis |
| 3 | 3% | 1:00 | F | Blood oozing |
| 4 | 3% | 2:00 | P | Continuous hemorrhage from aorta |
| 5 | 1% | 2:00 | G | Complete hemostasis |
| 6 | 1% | 2:00 | G | Complete hemostasis |

EXAMPLE 3

Hemostatic Effect of Aqueous Peptide Solution in Abdominal Aorta Injection Needle Perforation Model of Rabbits with Suppressed Blood Clotting Function The hemostatic effect of an aqueous peptide solution in rabbits administered an anticoagulant (heparin) was evaluated in an abdominal aorta injection needle perforation model.

<Materials>

Aqueous Peptide Solution

3% Aqueous peptide solution (peptide sequence: Ac-(RADA)$_4$-NH$_2$ (SEQ ID NO:1), CPC Scientific, Inc.)

Animals

Japanese white rabbits (3.0-4.0 kg, Japan White, conventional, purchased from Funabashi Farm Co., Ltd.). The animals were bred with breeding pellets (JA Higashinihon Kumiai Shiryou) supplied in a breeding room controlled to a room temperature of 25° C., a humidity of 65% and an illumination time of 12 hours (7:00-19:00), and water freely supplied with a water bottle. Fasting was from the morning of the test day, with water freely supplied.

<Method>

The rabbits were subcutaneously administered (3 mg/kg) Celactar 2% injection (2.0 g content as xylazine in 100 mL, product of Bayer Ltd.), and then ketamine (50 mg content as ketamine in 1 mL, product of Fuji Chemical Industries, Ltd.) was intravenously administered (10 mg/kg) for anesthesia.

1,000 units of heparin (Novo-Heparin for injection, 5000 units, Mochida Pharmaceutical Co., Ltd.) was administered through the inferior vena cava to artificially lower blood clotting function.

The rabbits were laparotomized by median section. Approximately 10 cm of the abdominal aorta was exposed, the blood vessel was ablated from the surrounding tissue, and the vessel was punctured with a 26G, 25G or 23G injection needle (Terumo Corp.).

Upon confirming hemorrhage, blood flow at the peripheral end and center end was clamped with a hemostatic clamp, and after removing the hemorrhaged blood with physiological saline and gauze, it was immediately treated with the aqueous peptide solution.

After 1-2 minutes of treatment, blood flow was released and the presence of hemorrhage was visually examined.

<Results>

Figure 4:
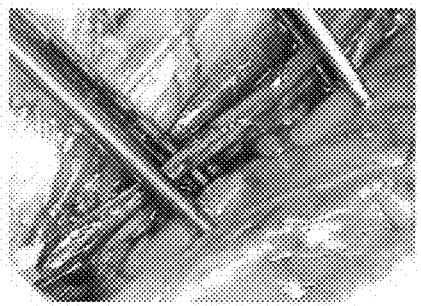
FIG. 4 shows the hemostatic effect of a 3% aqueous peptide solution in a abdominal aorta injection needle perforation model of rabbits with suppressed blood clotting function. (a) Condition before aortal puncture, (b) perivascular hemorrhage observed after aortal puncture (arrow tip), (c) coating aqueous peptide solution, (d) perivascular hemorrhage of (b) not seen after declamp (arrow tip).
Figure 4:
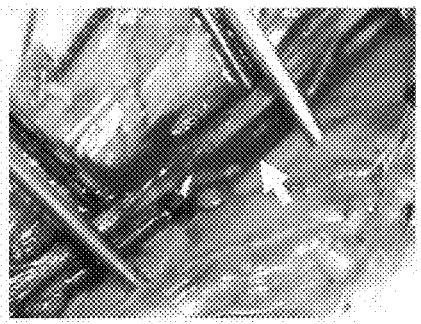
Figure 4:
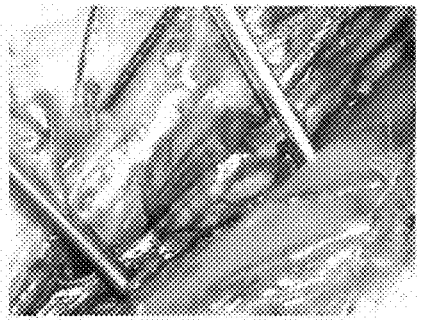
Figure 4:
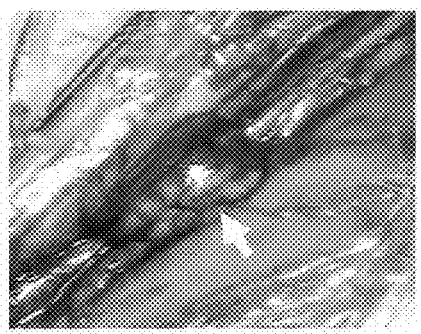

FIG. 4 shows the hemostatic effect of the aqueous peptide solution on hemorrhage from the abdominal aorta of rabbits with reduced blood clotting function in this example. As seen in Table 3, complete hemostasis was observed with 3% aqueous peptide solution in the 26G, 25G and 23G injection needle perforation models.

TABLE 3

| No. | Needle size (G) | Procedure time | Result | Observations |
|---|---|---|---|---|
| 1 | 23G | 1:00 | G | Complete hemostasis |
| 2 | 25G | 1:00 | G | Complete hemostasis |
| 3 | 25G | 1:00 | G | Complete hemostasis |
| 4 | 26G | 2:00 | G | Complete hemostasis |

EXAMPLE 4

Hemostatic Effect of Sugar-Containing Aqueous Peptide Solutions in Rabbit Abdominal Aorta/Portal Vein Stem Injection Needle Perforation Model The hemostatic effects of sugar-containing aqueous peptide solutions were evaluated using an abdominal aorta/portal vein stem injection needle perforation model.

<Materials>

Aqueous Peptide Solutions

1. Saccharose-containing aqueous peptide solutions (peptide sequence: Ac-(RADA)$_4$-NH$_2$ (SEQ ID NO:1), CPC Scientific, Inc; concentrations: 2% and 3%, saccharose: Wako Pure Chemical Industries, Ltd., 10% concentration)

2. Glucose-containing 2% aqueous peptide solution (peptide sequence: Ac-(RADA)$_4$-NH$_2$ (SEQ ID NO:1), CPC Scientific, Inc; glucose: Wako Pure Chemical Industries, Ltd., 5% concentration)

3. Trehalose-containing 2% aqueous peptide solution (peptide sequence: Ac-(RADA)$_4$-NH$_2$ (SEQ ID NO:1), CPC Scientific, Inc; trehalose: Wako Pure Chemical Industries, Ltd., 5% concentration)

4. 3% Aqueous peptide solution (peptide sequence: Ac-(RADA)$_4$-NH$_2$ (SEQ ID NO:1), CPC Scientific, Inc.)

5. 2% Aqueous peptide solution (peptide sequence: Ac-(RADA)$_4$-NH$_2$ (SEQ ID NO:1), CPC Scientific, Inc.)

Animals

Japanese white rabbits (3.0-4.0 kg, Japan White, conventional, purchased from Funabashi Farm Co., Ltd.). The animals were bred with breeding pellets (JA Higashinihon Kumiai Shiryou) supplied in a breeding room controlled to a room temperature of 25° C., a humidity of 65% and an illumination time of 12 hours (7:00-19:00), and water freely supplied with a water bottle. Fasting was from the morning of the test day, with water freely supplied.

<Method>

The rabbits were subcutaneously administered (3 mg/kg) Celactar 2% injection (2.0 g content as xylazine in 100 mL, product of Bayer Ltd.), and then ketamine (50 mg content as ketamine in 1 mL, product of Fuji Chemical Industries, Ltd.) was intravenously administered (10 mg/kg) for anesthesia.

The rabbits were laparotomized by median section. Approximately 10 cm of the abdominal aorta and portal vein stem was exposed, each blood vessel was ablated from the surrounding tissue, and the abdominal aorta was punctured with a 26G, 25G or 23G injection needle (Terumo Corp.) while the portal vein stem was punctured with a 26G injection needle (Terumo Corp.).

Upon confirming hemorrhage, blood flow at the peripheral end and center end was clamped with a hemostatic clamp, and after removing the hemorrhaged blood with physiological saline and gauze, it was immediately treated with the aqueous peptide solution.

After 1-2 minutes of treatment, blood flow was released and the presence of hemorrhage was visually examined.

<Results>

Figure 5:
FIG. 5 shows the hemostatic effect of a saccharose-containing 3% aqueous peptide solution in a abdominal aorta injection needle perforation model. (a) Condition before aortal puncture, (b) perivascular hemorrhage observed after aortal puncture (arrow tip), (c) coating aqueous peptide solution, (d) perivascular hemorrhage of (b) not seen after declamp (arrow tip).
Figure 5:
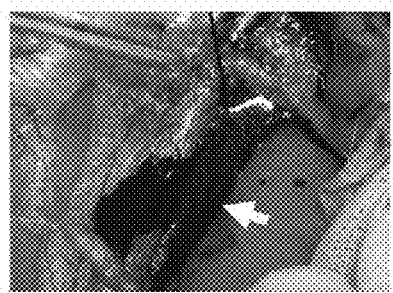
Figure 5:
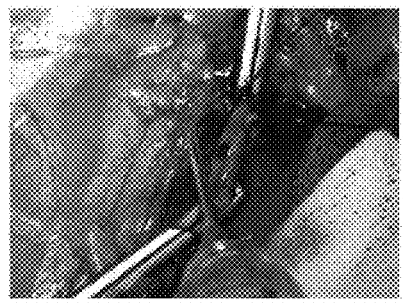
Figure 5:
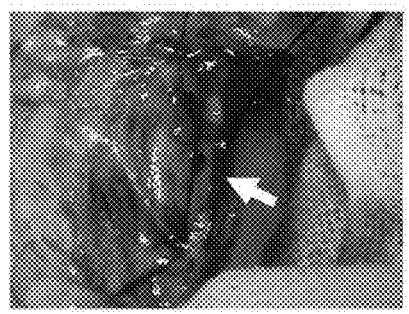

FIG. 5 shows the hemostatic effect of a sugar-containing aqueous peptide solution on hemorrhage from a blood vessel in this example. As seen in Table 4, the hemostatic effect of the saccharose-containing 3% aqueous peptide solution was equivalent to that of 3% aqueous peptide solution in the abdominal aorta 23G, 25G and 26G injection needle perforation models.

As seen in Table 5, the hemostatic effects of 2% aqueous peptide solution, saccharose-containing 2% aqueous peptide solution, glucose-containing 2% aqueous peptide solution and trehalose-containing 2% aqueous peptide solution were equivalent in the portal vein stem 26G injection needle perforation model.

TABLE 4

| No. | Aqueous peptide solution | Puncture site | Needle size (G) | Procedure time | Result | Observation |
|---|---|---|---|---|---|---|
| 1 | 3% | Abdominal aorta | 23 | 1:00 | G | Complete hemostasis |
| 2 | 3% | Abdominal aorta | 23 | 1:00 | G | Complete hemostasis |

TABLE 4-continued

| No. | Aqueous peptide solution | Puncture site | Needle size (G) | Procedure time | Result | Observation |
|---|---|---|---|---|---|---|
| 3 | 3% | Abdominal aorta | 25 | 1:00 | G | Complete hemostasis |
| 4 | 3% | Abdominal aorta | 25 | 1:00 | G | Complete hemostasis |
| 5 | 3% | Abdominal aorta | 25 | 1:00 | G | Complete hemostasis |
| 6 | 3% | Abdominal aorta | 26 | 2:00 | G | Complete hemostasis |
| 7 | Saccharose-containing 3% | Abdominal aorta | 23 | 2:00 | G | Complete hemostasis |
| 8 | Saccharose-containing 3% | Abdominal aorta | 23 | 1:00 | G | Complete hemostasis |
| 9 | Saccharose-containing 3% | Abdominal aorta | 23 | 2:00 | G | Complete hemostasis |
| 10 | Saccharose-containing 3% | Abdominal aorta | 23 | 2:00 | P | Projectile hemorrhage |
| 11 | Saccharose-containing 3% | Abdominal aorta | 25 | 2:00 | G | Complete hemostasis |
| 12 | Saccharose-containing 3% | Abdominal aorta | 26 | 1:00 | G | Complete hemostasis |
| 13 | Saccharose-containing 3% | Abdominal aorta | 26 | 1:00 | G | Complete hemostasis |
| 14 | Saccharose-containing 3% | Abdominal aorta | 26 | 2:00 | G | Complete hemostasis |
| 15 | Saccharose-containing 3% | Abdominal aorta | 26 | 2:00 | G | Complete hemostasis |
| 16 | Saccharose-containing 3% | Abdominal aorta | 26 | 2:00 | G | Complete hemostasis |

TABLE 5

| No. | Aqueous peptide solution | Puncture site | Needle size (G) | Procedure time | Result | Observation |
|---|---|---|---|---|---|---|
| 1 | 2% | Portal vein stem | 26G | 2:00 | G | Complete hemostasis |
| 2 | 2% | Portal vein stem | 26G | 2:00 | G | Complete hemostasis |
| 3 | Glucose-containing 2% | Portal vein stem | 26G | 2:00 | G | Complete hemostasis |
| 4 | Glucose-containing 2% | Portal vein stem | 26G | 2:00 | G | Complete hemostasis |
| 5 | Glucose-containing 2% | Portal vein stem | 26G | 2:00 | P | Continuous hemorrhage |
| 6 | Saccharose-containing 2% | Portal vein stem | 26G | 2:00 | G | Complete hemostasis |
| 7 | Trehalose-containing 2% | Portal vein stem | 26G | 2:00 | G | Complete hemostasis |

EXAMPLE 5

Lung Leakage Blocking Effect of Saccharose-Containing Aqueous Peptide Solution in Rabbit Lung Leakage Model A rabbit lung leakage model was prepared, and the lung leakage blocking effects of a saccharose-containing 3% aqueous peptide solution and physiological saline were compared.

<Materials>

Aqueous Peptide Solutions

1. Saccharose-containing 3% aqueous peptide solution (peptide sequence: Ac-(RADA)$_4$-NH$_2$ (SEQ ID NO:1), CPC Scientific, Inc; saccharose: Wako Pure Chemical Industries, Ltd., concentration: 10%)

2. Physiological saline (product of Otsuka Pharmaceutical Factory, Inc.)

Animals

Japanese white rabbits (3.0-4.0 kg, Japan White, conventional, purchased from Funabashi Farm Co., Ltd.). The animals were bred with breeding pellets (JA Higashinihon Kumiai Shiryou) supplied in a breeding room controlled to a room temperature of 25° C., a humidity of 65% and an illumination time of 12 hours (7:00-19:00), and water freely supplied with a water bottle. Fasting was from the morning of the test day, with water freely supplied.

<Method>

The rabbits were subcutaneously administered (3 mg/kg) Celactar 2% injection (2.0 g content as xylazine in 100 mL, product of Bayer Ltd.), and then ketamine (50 mg content as ketamine in 1 mL, product of Fuji Chemical Industries, Ltd.) was intravenously administered (10 mg/kg) for anesthesia.

The rabbits were thoracotomized under respiratory assistance with an artificial respirator. The lungs were exposed and bluntly wounded with forceps to create lung leakage with hemorrhage.

After removing the hemorrhaged blood with physiological saline and gauze, the hemorrhage surface was treated with saccharose-containing 3% aqueous peptide solution and physiological saline.

Approximately 30 seconds after treatment, the presence of hemorrhage and air leakage from the lung leak in the physiological saline was visually confirmed.

<Results>

Figure 6:
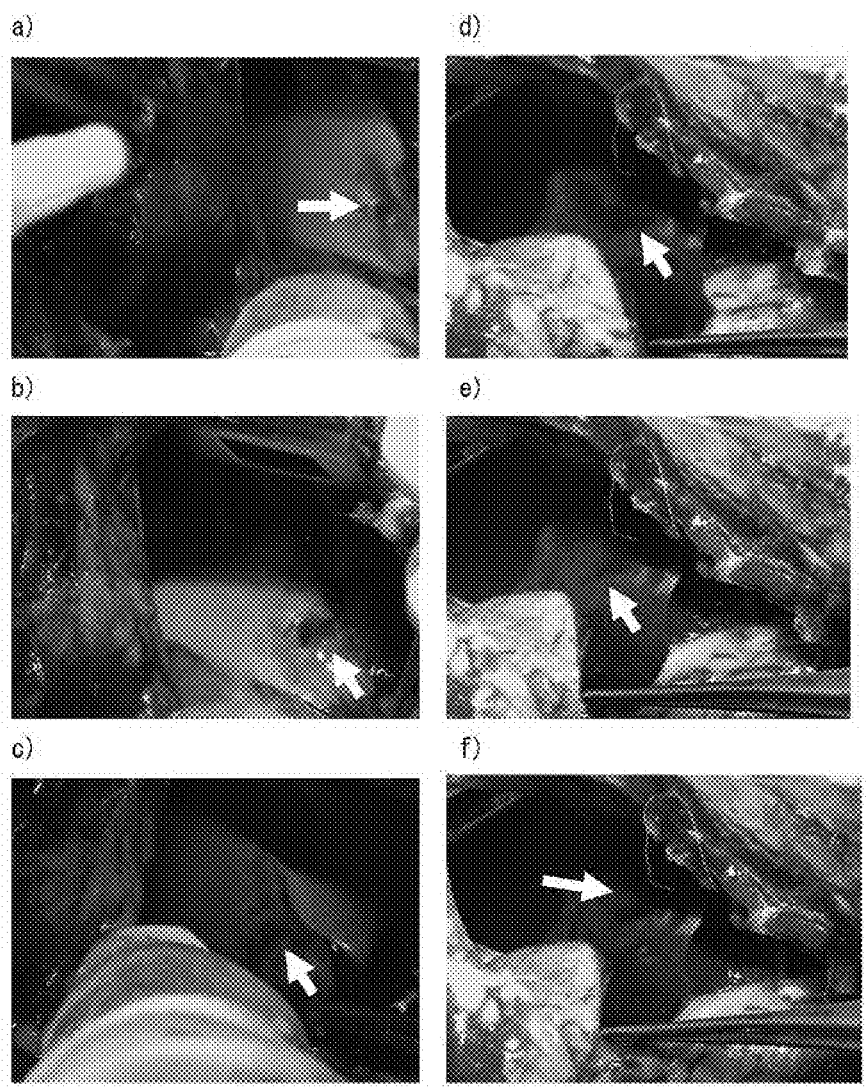
FIG. 6 shows a comparison of the hemostatic effects and lung leakage occlusion effects of saccharose-containing 3% aqueous peptide solution and physiological saline in a lung leakage model. (a) Hemorrhage confirmed in lung (arrow tip; saccharose-containing 3% aqueous peptide solution-treated group), (b) coating aqueous peptide solution (arrow tip; saccharose-containing 3% aqueous peptide solution-treated group), (c) wound site immersed in physiological saline to confirm air leaks, but no air leakage or hemorrhage observed (arrow tip; saccharose-containing 3% aqueous peptide solution-treated group), (d) hemorrhage confirmed in lung (arrow tip; physiological saline-treated group), (e) coating physiological saline (arrow tip; physiological saline-treated group), (f) no distinct hemorrhage since wound site was immersed in physiological saline to confirm air leaks, but continuous hemorrhage was observed (arrow tip; physiological saline-treated group).

FIG. 6 shows the lung leakage blocking effect of the saccharose-containing aqueous peptide solution in this example. As seen in Table 6, complete hemostasis and lung leak blockage were confirmed with saccharose-containing 3% aqueous peptide solution, but persistent hemorrhage and air leakage from the lung leak was observed with physiological saline.

TABLE 6

| Solution | Procedure time | Result | Remarks |
| --- | --- | --- | --- |
| Saccharose-containing 3% | 0:30 | G | Complete hemostasis. No air leakage from lung leak. |
| Physiological saline | — | P | Continuous hemorrhage and air leakage from lung leak. |

EXAMPLE 6

Bile Duct Wall Occlusion Effect of Aqueous Peptide Solution in Rabbit Bile Duct Injection Needle Perforation Model A rabbit injection needle bile duct perforation model was prepared, and the bile duct wall occlusion effect of an aqueous peptide solution was evaluated.

<Materials>

Aqueous Peptide Solution

3% Aqueous peptide solution (peptide sequence: Ac-(RADA)$_4$-NH$_2$ (SEQ ID NO:1), CPC Scientific, Inc.)

Animals

Japanese white rabbits (3.0-4.0 kg, Japan White, conventional, purchased from Funabashi Farm Co., Ltd.). The animals were bred with breeding pellets (JA Higashinihon Kumiai Shiryou) supplied in a breeding room controlled to a room temperature of 25° C., a humidity of 65% and an illumination time of 12 hours (7:00-19:00), and water freely supplied with a water bottle. Fasting was from the morning of the test day, with water freely supplied.

<Method>

The rabbits were subcutaneously administered (3 mg/kg) Celactar 2% injection (2.0 g content as xylazine in 100 mL, product of Bayer Ltd.), and then ketamine (50 mg content as ketamine in 1 mL, product of Fuji Chemical Industries, Ltd.) was intravenously administered (10 mg/kg) for anesthesia.

The rabbits were laparotomized by median section. Approximately 10 cm of the bile duct was exposed, and after ablation from the surrounding tissue, the bile duct was punctured with a 26G injection needle.

After confirming discharge of bile and continuous flow of bile, the bile flow was blocked with a hemostatic clamp.

The leaked bile was removed with physiological saline and gauze, and then treated with 3% aqueous peptide solution.

After 2 minutes of treatment, bile flow blockage was released and the presence of bile flow from the puncture site was visually examined.

<Results>

Figure 7:
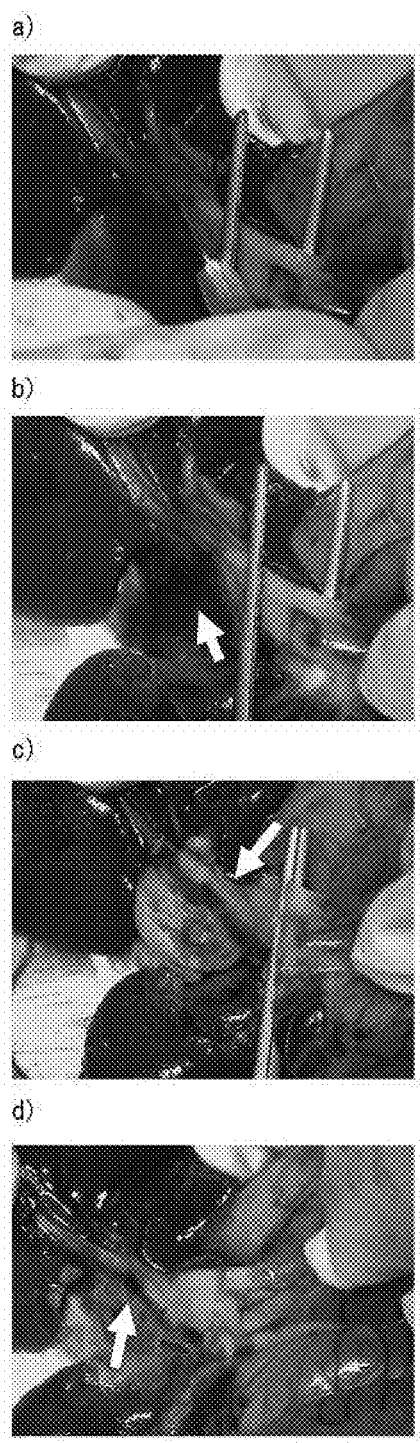
FIG. 7 bile duct wall occlusion effect of a 3% aqueous peptide solution in bile duct wall perforation model. (a) Condition before bile duct puncture, (b) bile leakage confirmed following bile duct puncture (arrow tip), (c) coating aqueous peptide solution (arrow tip), (d) bile leakage of (b) not observed around bile duct after rinsing with physiological saline (arrow tip).

FIG. 7 shows the bile duct wall occlusion effect of the aqueous peptide solution in this example. As seen in Table 7, a complete bile duct wall occlusion effect was observed with 3% aqueous peptide solution.

TABLE 7

| No. | Needle size (G) | Procedure time | Result | Observations |
| --- | --- | --- | --- | --- |
| 1 | 26G | 2:00 | G | Aqueous peptide solution gelled with bile, bile duct puncture site completely blocked |

EXAMPLE 7

Sustained Elevation of Excision Site and Hemostatic Effect of Aqueous Peptide Solution with Canine Intravesical Tumorectomy Aqueous peptide solutions were submucosally injected into the bladder during canine intravesical tumorectomy, and the sustained elevation and hemostatic effects of the aqueous peptide solutions at the excision site were evaluated.

<Materials>

Aqueous Peptide Solution

3% Aqueous peptide solution (peptide sequence: Ac-(RADA)$_4$-NH$_2$ (SEQ ID NO:1), CPC Scientific, Inc.)

Animals

Dogs (male)

<Method>

Canine intravesical tumorectomy was carried out under general anesthesia management, by the following procedure.

After hypogastric incision with an electrocautery scalpel (Erbe, Inc.), the electrocautery scalpel was used for incision of the bladder to expose the intravesical tumor (pedunculated tumor with a base site diameter of approximately 0.5 cm that iselevated from the vesical mucosa).

3% Aqueous peptide solution was submucosally injected around the tumor base in 4 injections of 0.5 mL each, and elevation of the tumor on the mucosa was confirmed.

After elevating the tumor, the tumor was excised with an electronic scalpel.

The time from aqueous peptide solution injection to complete tumor excision was approximately 2 minutes.

<Results>

Figure 8:
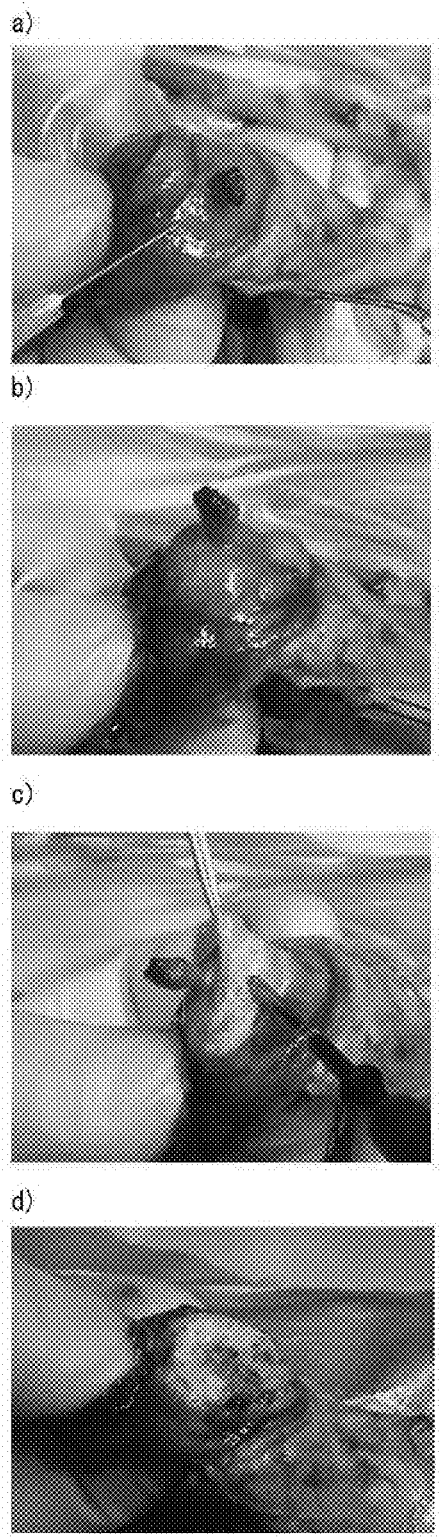
FIG. 8 shows mucosal swelling formation and hemostatic effect of a 3% aqueous peptide solution in an intravesical tumor. (a) Before infusion of aqueous peptide solution, (b) swelling of affected area confirmed after infusion of aqueous peptide solution, (c) no hemorrhage at excision site during tumor excision by electrocautery, (d) no hemorrhage at excision site after tumor excision by electrocautery.

As shown in FIG. 8, the tumors elevated by injection of aqueous peptide solution into the vesical mucosa, and the elevated state was maintained even during excision. No hemorrhage was observed either during or after tumor excision.

EXAMPLE 8

Hemostatic Effect of 2% Aqueous Peptide Solution in Rabbit Gastric Mucosa Incision Model A rabbit gastric mucosa incision hemorrhage model was prepared, and the hemostatic effect of a 2% aqueous peptide solution was evaluated.

<Materials>

Aqueous Peptide Solution 1. 2% Aqueous peptide solution (peptide sequence: Ac-(RADA)$_4$-NH$_2$ (SEQ ID NO:1), CPC Scientific, Inc.)

Animals

Japanese white rabbits (3.0-4.0 kg, Japan White, conventional, purchased from Funabashi Farm Co., Ltd.). The animals were bred with breeding pellets (JA Higashinihon Kumiai Shiryou) supplied in a breeding room controlled to a room temperature of 25° C., a humidity of 65% and an illumination time of 12 hours (7:00-19:00), and water freely supplied with a water bottle. Fasting was from the morning of the test day, with water freely supplied.

<Method>

The rabbits were subcutaneously administered (3 mg/kg) Celactar 2% injection (2.0 g content as xylazine in 100 mL, product of Bayer Ltd.), and then ketamine (50 mg content as ketamine in 1 mL, product of Fuji Chemical Industries, Ltd.) was intravenously administered (10 mg/kg) for anesthesia.

The rabbits were laparotomized by median section and the stomachs were incised, after which the gastric mucosa was exposed and sharply incised with a scalpel to about 1 cm to induce hemorrhage.

After confirming blood oozing from the incision, the blood was removed as much as possible with gauze and the gastric mucosa incision was treated with aqueous peptide solution.

The gelled aqueous peptide solution was removed 1 minute after treatment using physiological saline, and the presence of any hemorrhage from the gastric mucosa incision was visually confirmed.

<Results>

Figure 9:
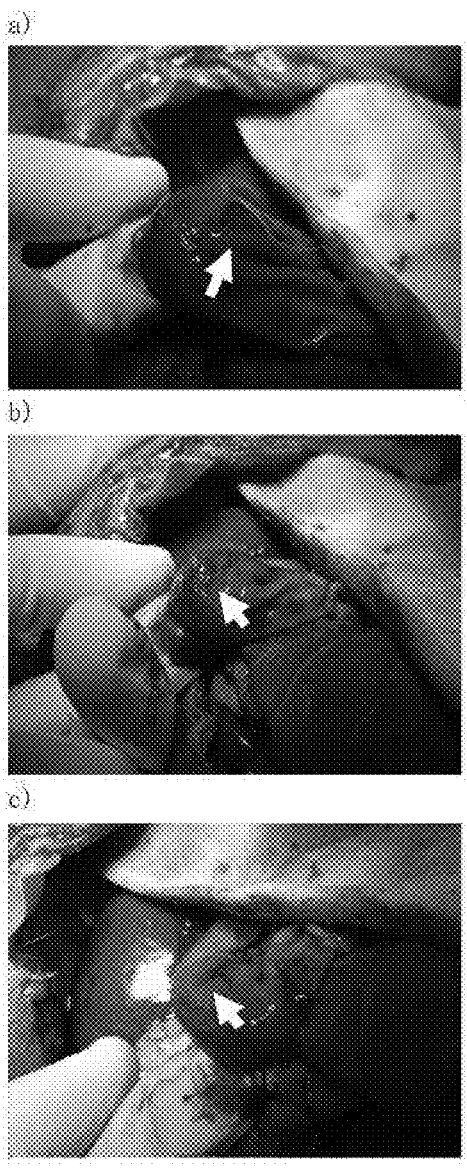
FIG. 9 shows the hemostatic effect of a 2% aqueous peptide solution in a gastric mucosa incision model. (a) hemorrhage confirmed after hepatic incision (arrow tip), (b)

FIG. 9 shows the hemostatic effect of the aqueous peptide solution on hemorrhage from the gastric mucosa incision in this example. No hemorrhage was observed after applying the aqueous peptide solution.

EXAMPLE 9

Hemostatic Effect of 1% Aqueous Peptide Solution in Rabbit Hepatic Transection Model A rabbit hepatic transection hemorrhage model was prepared, and the hemostatic effect of a 1% aqueous peptide solution was evaluated.

<Materials>

Aqueous Peptide Solutions 1. 1% Aqueous peptide solution (peptide sequence: IEIK9 (SEQ ID NO: 4), CPC Scientific, Inc)

2. 1% Aqueous peptide solution (peptide sequence: IEIK13 (SEQ ID NO: 2; SEQ ID NO:8), CPC Scientific, Inc)

3. 1% Aqueous peptide solution (peptide sequence: KLD (SEQ ID NO: 3; SEQ ID NO:11), CPC Scientific, Inc)

Animals

Japanese white rabbits (3.0-4.0 kg, Japan White, conventional, purchased from Funabashi Farm Co., Ltd.). The animals were bred with breeding pellets (JA Higashinihon Kumiai Shiryou) supplied in a breeding room controlled to a room temperature of 25° C., a humidity of 65% and an illumination time of 12 hours (7:00-19:00), and water freely supplied with a water bottle. Fasting was from the morning of the test day, with water freely supplied.

<Method>

The rabbits were subcutaneously administered (3 mg/kg) Celactar 2% injection (2.0 g content as xylazine in 100 mL, product of Bayer Ltd.), and then ketamine (50 mg content as ketamine in 1 mL, product of Fuji Chemical Industries, Ltd.) was intravenously administered (10 mg/kg) for anesthesia.

The rabbits were laparotomized by median section and the hepatic left lobes were exposed and sharply transected with a scalpel to about 1 cm to induce hemorrhage.

After confirming exudative hemorrhage from the incision, the blood was removed as much as possible with gauze and the hepatic incision was treated with aqueous peptide solution.

The gelled aqueous peptide solution was removed 1 minute after treatment using physiological saline, and the presence of any hemorrhage from the hepatic incision was visually confirmed.

<Results>

FIG. 10 shows the hemostatic effect of the aqueous peptide solution on hemorrhage from the hepatic incision in this example. Absolutely no gelling and no hemostatic effect was observed when the IEIK9 (SEQ ID NO:4; SEQ ID NO:9) aqueous peptide solution was used as the upper layer on the hemorrhage wound surface, but the IEIK13 (SEQ ID NO:2; SEQ ID NO:8) aqueous peptide solution and KLD SEQ ID NO:3; SEQ ID NO:11) aqueous peptide solution gelled after applying, and no hemorrhage was observed.

EXAMPLE 10

Self-Assembly of Aqueous Peptide Solution with Rabbit Bile

Self-assembly of aqueous peptide solutions with rabbit bile was evaluated with different aqueous peptide solutions.

<Materials>

Aqueous Peptide Solutions 1. 1.5% Aqueous peptide solution (peptide sequence: Ac-(RADA)$_4$-NH$_2$ (SEQ ID NO:1), CPC Scientific, Inc.)

2. 1% Aqueous peptide solution (peptide sequence: IEIK9 (SEQ ID NO:4; SEQ ID NO:9), CPC Scientific, Inc)

3. 1% Aqueous peptide solution (peptide sequence: IEIK13 (SEQ ID NO:2, SEQ ID NO:8), CPC Scientific, Inc)

4. 1% Aqueous peptide solution (peptide sequence: KLD (SEQ ID NO:3; SEQ ID NO:11), CPC Scientific, Inc)

Animals

Japanese white rabbits (3.0-4.0 kg, Japan White, conventional, purchased from Funabashi Farm Co., Ltd.). The animals were bred with breeding pellets (JA Higashinihon Kumiai Shiryou) supplied in a breeding room controlled to a room temperature of 25° C., a humidity of 65% and an illumination time of 12 hours (7:00-19:00), and water freely supplied with a water bottle. Fasting was from the morning of the test day, with water freely supplied.

<Method>

The rabbits were subcutaneously administered (3 mg/kg) Celactar 2% injection (2.0 g content as xylazine in 100 mL, product of Bayer Ltd.), and then ketamine (50 mg content as ketamine in 1 mL, product of Fuji Chemical Industries, Ltd.) was intravenously administered (10 mg/kg) for anesthesia.

The rabbits were laparotomized by median section, and bile was sampled from the gallbladder using a 23G injection needle (Terumo Corp.).

Droplets of each aqueous peptide solution before self-assembly were prepared (diameter: approximately 5-8 mm), and the sampled bile was gently poured thereover so as to cover the aqueous peptide solution.

After approximately 30 seconds the bile was removed and self-assembly was confirmed, and the self-assembled gel was physically disrupted with a 23G injection needle.

<Results>

FIG. 11 shows an example of self-assembly of the aqueous peptide solutions of this example by bile. Bile-induced self-assembly was confirmed in all of the aqueous peptide solutions except for IEIK9 (SEQ ID SEQ ID NO:9).

Example 11

Confirmation of Vascular Embolization Effect of 3% Aqueous Peptide Solution in Rat Portal Vein Embolization A 3% aqueous peptide solution was injected through the rat portal vein, and the vascular embolization effect was evaluated.

<Materials>

3% Aqueous peptide solution (peptide sequence: Ac-(RADA)$_4$-NH$_2$ (SEQ ID NO:1), CPC Scientific, Inc.)

Animals

SD rats (250 g, male, purchased from Japan SLC, Inc.) were raised in a breeding room controlled to temperature/humidity: 22±3° C./50±20%, ventilation frequency: 10-15 time/hr, illumination time: artificial illumination for 12 hours (8:00-20:00), and were given free access to solid feed CRF-1 (Oriental Yeast Co., Ltd.) using a metal feeder, with tap water made freely available using an automatic water supplier.

<Method>

The rats were subjected to inhalation anesthesia with diethyl ether (Kishida Chemical Co., Ltd.).

The rats were laparotomized by median section and the portal veins were exposed.

A 4 mL portion of aqueous peptide solution was injected through the portal vein stem with a 26G injection needle (Terumo Corp.), and hemorrhage from the puncture site was immediately arrested with aqueous peptide solution.

The livers were extracted 5 minutes after injection and immediately fixed with 10% formalin (Wako Pure Chemical Industries, Ltd.).

The tissue was stained with haematoxylin eosin (HE) 1 week after fixing.

<Results>

As shown in FIG. 12, portal vein embolization with aqueous peptide solution was confirmed.

EXAMPLE 12

Confirmation of Self-Assembly of Aqueous Peptide Solution Dissolving Iopamidol

Self-assembly of an aqueous peptide solution dissolving iopamidol was evaluated.

<Materials>

Aqueous Peptide Solution

3% Aqueous peptide solution (peptide sequence: Ac-(RADA)$_4$-NH$_2$ (SEQ ID NO:1), CPC Scientific, Inc.)

Cell culturing medium (Dulbecco's Modified Eagle Medium, Gibco)

Iopamidol (Wako Pure Chemical Industries, Ltd.)

<Method>

306.2 mg of iopamidol was dissolved in 1 ml of 3% aqueous peptide solution.

The iopamidol-containing 3% aqueous peptide solution was diluted with MilliQ water to prepare a 0.0468% aqueous peptide solution. A 300 µl portion of cell culturing medium was added in 6 portions, 50 µl at a time, to 100 µl of the 3% iopamidol-containing aqueous peptide solution and 0.0468% iopamidol-containing aqueous peptide solution, surrounding and contacting the 3% iopamidol-containing aqueous peptide solution and 0.0468% iopamidol-containing aqueous peptide solution. At 15 minutes after addition of the culture medium, the surrounding culture medium was removed and gellation was visually confirmed.

<Results>

As shown in FIG. 13, self-assembly was confirmed with the iopamidol-containing aqueous peptide solutions.

EXAMPLE 13

Confirmation of Self-Assembly of Iopamidol-Containing 3% Aqueous Peptide Solution after Microcatheter Passage Self-assembly of a 3% aqueous peptide solution dissolving iopamidol was evaluated.

<Materials>

Aqueous Peptide Solution

3% Aqueous peptide solution (peptide sequence: Ac-(RADA)$_4$-NH$_2$ (SEQ ID NO:1), CPC Scientific, Inc.)

Cell culturing medium (Dulbecco's Modified Eagle Medium, Gibco)

Iopamidol (Wako Pure Chemical Industries, Ltd.)

Microcatheter (2.4 Fr, 150/20, Boston Scientific)

<Method>

306.2 mg of iopamidol was dissolved in 1 ml of 3% aqueous peptide solution.

The iopamidol-containing 3% aqueous peptide solution was discharged into the cell culturing medium through a catheter.

<Results>

As shown in FIG. 14, self-assembly was confirmed with the iopamidol-containing 3% aqueous peptide solution.

The invention claimed is:

1. A liquid composition comprising a peptide that consists of SEQ ID NO:2, the composition being characterized by an ability to occlude sites of tissue damage in mammals, wherein the liquid composition gels by self-assembly into a β-sheet structure at physiological pH in the presence of monovalent alkali metal ions.

2. The liquid composition of claim 1, further comprising a small molecule drug.

3. The liquid composition of claim 2, wherein the small molecule drug is selected from the group consisting of glucose, saccharose, purified saccharose, lactose, maltose, trehalose, dextran, iodine, lysozyme chloride, dimethylisopropylazulene, tretinoin tocoferil, povidone iodine, alprostadil alfadex, anise alcohol, isoamyl salicylate, α,α-dimethylphenylethyl alcohol, bacdanol, helional, sulfazin silver, bucladesine sodium, alprostadil alfadex, gentamycin sulfate, tetracycline hydrochloride, sodium fusidate, mupirocin calcium hydrate and isoamyl benzoate.

4. The liquid composition of claim 1, wherein the peptide is present at a concentration from 1% to 3%.

\* \* \* \* \*